(12) United States Patent
Chaput et al.

(10) Patent No.: US 8,389,467 B2
(45) Date of Patent: Mar. 5, 2013

(54) IN SITU SELF-SETTING MINERAL-POLYMER HYBRID MATERIALS, COMPOSITION AND USE THEREOF

(75) Inventors: Cyril Chaput, Montreal (CA); Anabelle Rodrigues El Zein, Montreal-Nord (CA)

(73) Assignee: Piramal Healthcare (Canada) Ltd., Aurora (CA)

( * ) Notice: Subject to any disclaimer, the term of this patent is extended or adjusted under 35 U.S.C. 154(b) by 193 days.

(21) Appl. No.: 12/575,765

(22) Filed: Oct. 8, 2009

(65) Prior Publication Data

US 2010/0029549 A1 Feb. 4, 2010

Related U.S. Application Data

(63) Continuation of application No. 10/149,052, filed as application No. PCT/CA00/01489 on Dec. 8, 2000, now abandoned.

(60) Provisional application No. 60/169,954, filed on Dec. 9, 1999.

(51) Int. Cl.
 *A61K 38/16* (2006.01)
(52) U.S. Cl. ..................... 514/1.1; 623/23.61
(58) Field of Classification Search .................. None
 See application file for complete search history.

(56) References Cited

U.S. PATENT DOCUMENTS

| | | |
|---|---|---|
| 4,185,618 A | 1/1980 | Corey |
| 4,391,909 A | 7/1983 | Lim |
| 4,394,373 A | 7/1983 | Malette et al. |
| 4,424,346 A | 1/1984 | Hall et al. |
| 4,474,769 A | 10/1984 | Smith |
| 4,647,536 A | 3/1987 | Mosbach et al. |
| 4,659,700 A | 4/1987 | Jackson |
| 4,722,948 A | 2/1988 | Sanderson |
| 4,731,081 A | 3/1988 | Tiffany et al. |
| 4,803,075 A | 2/1989 | Wallace et al. |
| 4,895,724 A | 1/1990 | Cardinal et al. |
| 4,956,350 A | 9/1990 | Mosbey |
| 4,996,307 A | 2/1991 | Ito et al. |
| 5,073,202 A | 12/1991 | Wallach et al. |
| 5,126,141 A | 6/1992 | Henry |
| 5,266,326 A | 11/1993 | Barry et al. |
| 5,278,201 A | 1/1994 | Dunn et al. |
| 5,318,780 A | 6/1994 | Viegas et al. |
| 5,368,051 A | 11/1994 | Dunn et al. |
| 5,422,116 A | 6/1995 | Yen et al. |
| 5,468,787 A | 11/1995 | Braden et al. |
| 5,489,401 A | 2/1996 | Freeman |
| 5,587,175 A | 12/1996 | Viegas et al. |
| 5,599,552 A | 2/1997 | Dunn et al. |
| 5,612,028 A | 3/1997 | Sackier et al. |
| 5,618,339 A | 4/1997 | Ito |
| 5,620,706 A | 4/1997 | Dumitriu et al. |
| 5,626,861 A | 5/1997 | Laurencin et al. |
| 5,655,546 A | 8/1997 | Halpern |
| 5,658,593 A | 8/1997 | Orly et al. |
| 5,709,854 A | 1/1998 | Griffith-Cima et al. |
| 5,723,331 A | 3/1998 | Tubo et al. |
| 5,736,372 A | 4/1998 | Vacanti et al. |
| 5,749,874 A | 5/1998 | Schwartz |
| 5,770,193 A | 6/1998 | Vacanti et al. |
| 5,770,417 A | 6/1998 | Vacanti et al. |
| 5,773,033 A | 6/1998 | Cochrum et al. |
| 5,773,608 A | 6/1998 | Yen et al. |
| 5,811,094 A | 9/1998 | Caplan et al. |
| 5,820,608 A | 10/1998 | Luzio et al. |
| 5,837,235 A | 11/1998 | Mueller et al. |
| 5,842,477 A | 12/1998 | Naughton et al. |
| 5,855,619 A | 1/1999 | Caplan et al. |
| 5,866,415 A | 2/1999 | Villeneuve |
| 5,871,985 A | 2/1999 | Aebischer et al. |
| 5,894,070 A | 4/1999 | Hansson et al. |
| 5,902,741 A | 5/1999 | Purchio et al. |
| 5,902,798 A | 5/1999 | Gouda et al. |
| 5,906,934 A | 5/1999 | Grande et al. |
| 5,908,784 A | 6/1999 | Johnstone et al. |
| 5,944,754 A | 8/1999 | Vacanti |
| 5,958,443 A | 9/1999 | Viegas et al. |
| 5,977,330 A | 11/1999 | Lohmann et al. |
| 6,005,161 A | 12/1999 | Brekke et al. |
| 6,060,534 A | 5/2000 | Ronan et al. |
| 6,080,194 A | 6/2000 | Pachence et al. |

(Continued)

FOREIGN PATENT DOCUMENTS

| | | |
|---|---|---|
| EP | 0 298 501 A | 1/1989 |
| EP | 0 640 647 A2 | 3/1995 |

(Continued)

OTHER PUBLICATIONS

Aerts et al., *Journal of Biomechanics*, 28(11):1299-1308 (1995).
Aiba, *Makromol. Chemie*, 194(1):65-75 (1993).
Alexander et al., *Journal of Zoology—London (A)*, 209:405-419 (1986).
Appling et al., *FEBS Letters*, 250(2):541-544 (1989).
Aspden et al., *European Journal of Pharmaceutical Sciences*, 4:23-31 (1996).
Aston et al., *Journal of Bone and Joint Surgery*, 68-B(1):29-35 (1986).

(Continued)

*Primary Examiner* — Christopher R. Tate
*Assistant Examiner* — Roy Teller
(74) *Attorney, Agent, or Firm* — Nixon Peabody LLP; David S. Resnick; Leena H. Karttunen Contarino

(57) ABSTRACT

The present invention relates to self-setting compositions consisting in admixed liquid and solid components enable the formation of hardened bio-materials having a broad range of properties and performances. The present invention proposes a) a thermo-sensitive self-gelling liquid component, being water-based, comprising at least a polycationic and a phosphate source, wherein the liquid component is a thermo-gelling solution at a pH ranging from 6.5 to 7.4; b) a powder component consisting in at least two calcium phosphate sources. The preferred calcium phosphate source includes apatites, tricalcium phosphates, tetracalcium phosphates and dicalcium phosphates. Both solid and liquid components are admixed to form a flowable slurry that sets in situ into a hardened calcium phosphate based bio-material.

10 Claims, 5 Drawing Sheets

U.S. PATENT DOCUMENTS

| | | | |
|---|---|---|---|
| 6,110,209 | A | 8/2000 | Stone |
| 6,124,273 | A | 9/2000 | Drohan et al. |
| 6,136,334 | A | 10/2000 | Viegas et al. |
| 6,179,872 | B1 | 1/2001 | Bell et al. |
| 6,200,606 | B1 | 3/2001 | Peterson et al. |
| 6,344,488 | B1 * | 2/2002 | Chenite et al. ............... 514/777 |
| 6,372,257 | B1 * | 4/2002 | Marchosky ................ 424/488 |
| 6,417,247 | B1 * | 7/2002 | Armstrong et al. .......... 523/115 |
| 6,610,669 | B1 | 8/2003 | Calias et al. |
| 6,649,192 | B2 | 11/2003 | Alonso Fernandez et al. |
| 6,706,690 | B2 | 3/2004 | Reich et al. |
| 6,743,783 | B1 | 6/2004 | Vournakis et al. |
| 6,756,363 | B1 | 6/2004 | Nordquist et al. |
| 6,911,212 | B2 | 6/2005 | Gertzman |
| 7,045,141 | B2 | 5/2006 | Merboth |
| 7,148,209 | B2 | 12/2006 | Hoemann et al. |
| 7,320,962 | B2 | 1/2008 | Reich et al. |
| 7,368,126 | B2 | 5/2008 | Chen et al. |
| 7,459,307 | B2 | 12/2008 | Ha et al. |
| 2002/0082220 | A1 | 6/2002 | Hoemann et al. |
| 2003/0143274 | A1 | 7/2003 | Viegas et al. |
| 2003/0147860 | A1 | 8/2003 | Marchosky |
| 2003/0158302 | A1 | 8/2003 | Chaput et al. |
| 2003/0199615 | A1 | 10/2003 | Chaput et al. |
| 2004/0022859 | A1 | 2/2004 | Chen et al. |
| 2004/0024069 | A1 | 2/2004 | Chen et al. |
| 2004/0047892 | A1 | 3/2004 | Desrosiers et al. |
| 2004/0091540 | A1 | 5/2004 | Desrosiers et al. |
| 2006/0018973 | A1 | 1/2006 | Kim et al. |
| 2006/0062768 | A1 | 3/2006 | Hnojewyj |
| 2006/0193892 | A1 | 8/2006 | Furst et al. |
| 2006/0204544 | A1 | 9/2006 | Sunwoo et al. |
| 2006/0204581 | A1 | 9/2006 | Gower et al. |
| 2006/0293216 | A1 | 12/2006 | Klaveness et al. |
| 2007/0014867 | A1 | 1/2007 | Kusanagi et al. |
| 2007/0037737 | A1 | 2/2007 | Hoemann et al. |
| 2007/0167400 | A1 | 7/2007 | Boucher et al. |
| 2007/0254007 | A1 | 11/2007 | Bumgardner et al. |
| 2008/0118563 | A1 | 5/2008 | Muzzarelli et al. |
| 2008/0200430 | A1 | 8/2008 | Bitterman et al. |
| 2008/0248991 | A1 | 10/2008 | Dyer et al. |
| 2009/0004276 | A1 | 1/2009 | Ben-Shalom et al. |

FOREIGN PATENT DOCUMENTS

| | | | |
|---|---|---|---|
| EP | 1 077 253 | A1 | 2/2001 |
| WO | WO 95/25549 | | 9/1995 |
| WO | WO 96/02276 | | 2/1996 |
| WO | WO 96/39202 | | 12/1996 |
| WO | WO 97/33562 | | 9/1997 |
| WO | WO 98/22114 | | 5/1998 |
| WO | WO 99/04720 | | 2/1999 |
| WO | WO 99/07416 | | 2/1999 |
| WO | WO 99/47186 | | 9/1999 |
| WO | WO 00/02905 | | 1/2000 |
| WO | WO 00/44413 | | 8/2000 |
| WO | WO 00/48550 | | 8/2000 |
| WO | 01/06000 | A1 | 5/2001 |
| WO | WO 01/36000 | A1 | 5/2001 |
| WO | WO 01/41822 | A1 | 6/2001 |
| WO | 02/00272 | A2 | 1/2002 |
| WO | WO 02/40070 | A2 | 5/2002 |
| WO | 2008/064487 | A1 | 6/2008 |
| WO | 2004/016297 | A1 | 2/2010 |

OTHER PUBLICATIONS

Ateshian, *Journal of Biomechanical Engineering*, 119:81-86 (1997).
Austin et al., *Science*, 212:749-753 (1981).
Back et al., *Biochemistry*, 18(23):5191-5196 (1979).
Balkin, *Neale's Common Foot Disorders: Diagnosis and Management*, 22:387-400 (1997).
Bartone et al., *Journal of Urology*, 140:1134-1137 (1988).
Bellows et al., *Bone and Mineral*, 17:15-29 (1992).
Bennett et al., *Journal of Anatomy*, 171:131-138 (1990).
Bentley et al., *Nature*, 230:385-388 (1971).
Bernkop-Schnurch et al., *Journal of Pharmaceutical Sciences.* 87(4):430-434 (1998).
Blechschmidt, *Foot and Ankle*, 2(5):260-283 (1982).
Bobic et al., *The Journal of Bone and Joint Surgery*, 82-B(2):165-166 (2000).
Breinan et al., *The Journal of Bone and Joint Surgery*, 79-A(10):1439-1451 (1997).
Breinan et al., *Journal of Orthopaedic Research*, 18(5):781-789 (2000).
Gillquist et al., *Acta Orthop Scand.*, 68(2):186-191 (1997).
Brittberg et al., *The New England Journal of Medicine*, 331(14):889-895 (1994).
Brittberg et al., *Clinical Orthopaedics and Related Research*, 326:270-283 (1996).
Buckwalter et al., *The Journal of Bone and Joint Surgery*, 79-A(4):612-632 (1997).
Buschmann et al., *Journal of Orthopaedic Research*, 10(6):745-758 (1992).
Buschmann et al., *Foot and Ankle*, 14(7):389-394 (1993).
Buschmann et al., *Foot and Ankle*, 16(5):254-258 (1995).
Butnariu-Ephrat et al., *Clinical Orthopaedics and Related Research*, 330:234-243 (1996).
Calvo et al., *Colloid and Polymer Science*, 275(1):46-53 (1997) (abstract).
Caplan et al., *Clinical Orthopaedics and Related Research*, 342:254-269 (1997).
Carreño-Gómez et al., *International Journal of Pharmaceutics*, 148:231-240 (1997).
Chenite et al., *Carbohydrate Polymers*, 00:1-9 (2000).
Chentte et al., *Biomaterials*, 21:2155-2161 (2000).
Chesterman et al., *The Journal of Bone and Joint Surgery*, 50B(1):184-197 (1968).
Childers et al., *Clinical Orthopaedics and Related Research*, 144:114-120 (1979).
Cho et al., *Biomaterials*, 20:2139-2145 (1999).
Chu et al., *Journal of Biomedical Materials Research*, 29:1147-1154 (1995).
Chu et al., *Clinical Orthopaedics and Related Research*, 340:220-229 (1997).
Chung et al., *Calcif Tissue Int.*, 51:305-311 (1992).
Cohen et al., *British Journal of Haemotology*, 31:45-50 (1975).
D'Ambrosia, *Orthopedics*, 10(1):137-142 (1987).
Denuziere et al., *Biomaterials*, 19:1275-1285 (1998).
DePalma et al., *Clinical Orthopaedics and Related Research*, 48:229-242 (1966).
Dillon et al., *J. Biomater. Sci. Polymer Edn.*, 9(10):1049-1069 (1998).
Elçin et al., *Neurological Research*, 20:648-654 (1998).
Frenkel et al., *The Journal of Bone and Joint Surgery*, 79-B(5):831-836 (1997).
Freed et al., *Journal of Biomedical Materials Research*, 28:891-899 (1994).
Fukamizo et al., *Biochem. Cell Biol.*, 75:687-696 (1997).
Grande et al., *Journal of Orthopaedic Research*, 7(2):208-218 (1989).
Green, *Clinical Orthopaedics and Related Research*, 124:237-250 (1977).
Guo et al., Connective Tissue Research, 19:277-297 (1989).
Gupta et al., *The International Journal of Artificial Organs*, 16(3):155-163 (1993).
Hangody et al., *Knee Surg., Sports Traumatol., Arthrosc.*, 5:262-267 (1997).
Hangody et al., *Foot and Ankle International*, 18(10):628-634 (1997).
Hendrickson et al., *Journal of Orthopaedic Research*, 12(4):485-497 (1994).
Higaki et al., *JSME International Journal*, 40(4):776-781 (1997).
Hirano et al., *Biopolymers*, 15:1685-1691 (1976).
Homminga et al., *Acta Orthop. Scand.*, 62(5):415-418 (1991).
Hunziker et al., *The Journal of Bone and Joint Surgery*, 78-A(5):721-733 (1996).
Hyc et al., *Cell Transplantation*, 6(2):119-124 (1997).
Itay et al., *Cartilage Repair by Cultured Chondrocytes*, 220:284-303 (1987).
Jahss et al., *Foot and Ankle*, 13(5):227-232 (1992).
Johnson, *Operative Arthroscopy*, Chapter 24, pp. 341-360 (1991).

Jürgensen et al., *The Journal of Bone and Joint Surgery*, 79-A(2):185-193 (1997).
Kandel et al., *Art. Cells, Blood Subs., and Immob. Biotech.*, 23(5):565-577 (1995).
Kawamura et al., *Acta Orthop. Scand.*, 69(1):56-62 (1998).
Ker, *Journal of Experimental Biology*, 199:1501-1508 (1996).
Kopp et al., *Int. J. Cancer*, 60:275-279 (1995).
Koyano et al., *J. Biomed. Mater. Res.*, 39:486-490 (1998).
Kubota et al., *Polymer Journal*, 29(2):123-127 (1997).
Kuettner, *Clinical Biochemistry*, 25:155-163 (1992).
Lahiji et al., *J. Biomed. Mater. Res.*, 51:586-595 (2000).
Lee et al., *Journal of Controlled Release*, 51:213-220 (1998).
Lee et al., *J. Periodontol.*, 71(3):410-417 (2000).
Leistikow, *Seminars in Thrombosis and Hemostasis*, 22(3):289-294 (1996).
Li, *Biotechnol. Appl. Biochem.*, 23:269-271 (1996).
Lu et al., *Biomaterials*, 20:1937-1944 (1999).
Mahomed et al., *Orthopedics*, 15(10):1191-1199 (1992).
Malette et al., *The Annals of Thoracic Surgery*, 36(1):55-58 (1983).
Mankin, The New England Journal of Medicine, pp. 1285-1292 (1974).
Matthew et al., *Journal of Pediatric Surgery*, 28(11):1423-1428 (1993).
Mattioli-Belmonte et al., *Medical and Biological Engineering and Computing*, 37:130-134 (1999).
Messner et al., *Acta Orthop. Scund.*, 67(5):523-529 (1996).
Minas et al., *Articular Cartilage Defects*, 20(6):525-538 (1997).
Muzzarelli et al., *Biomaterials*, 9:247-252 (1988).
Muzzarelli et al., *Eur. Chitin Soc.*, Ancona (1993).
Muzzarelli et al., *Biomaterials*, 15(13):1075-1081 (1994).
Muzzarelli et al., *Enzyme Microb. Technol.*, 17:541-545 (1995).
Namba et al., *The Journal of Bone and Joint Surgery*, 80-A(1):4-10 (1998).
Narváez et al., *Radiographics*, 20(2):333-352 (2000).
Nevo et al., *Cell Transplantation*, 7(1):63-70 (1998).
Newman, *The American Journal of Sports Medicine*, 26(2):309-324 (1998).
Nixon et al., Journal of Orthopaedic Research, 17(4):475-487 (1999).
Noguchi et al., *Clinical Orthopaedics and Related Research*, 302:251-258 (1994).
O'Driscoll et al., *The Journal of Bone and Joint Surgery*, 70-A(4):595-606 (1988).
O'Driscoll, et al., *The Journal of Bone and Joint Surgery*, 76-A(7):1042-1051 (1994).
Ohya et al., *J. Microencapsulation*, 10(1):1-9 (1993).
Okamoto et al., *J. Vet. Med. Sci.*, 57(5):851-854 (1995).
Outerbridge et al., *The Journal of Bone and Joint Surgery*, 77-A(1):65-72 (1995).
Paletta et al., *The American Journal of Sports Medicine*, 20(6):725-731 (1992).
Pechak et al., *Bone*, 7:459-472 (1986).
Peluso et al., *Biomaterials*, 15(15):1215-1220 (1994).
Pridie, *The Journal of Bone and Joint Surgery*, 41-B(3):618-619 (1959).
Rao et al., *Journal of Biomedical Materials Research*, 34:21-28 (1997).
Robinson et al., *Calcif Tissue Int.*, 46:246-253 (1990).
Rodrigo et al., Operative Orthopaedics, Chapter 144, pp. 2077-2082 (1993).
Sall et al., *Ann. Ophthalmol.*, 19:31-33 (1987).
Sams et al., *Osteoarthritis and Cartilage*, 3:47-59 (1995).
Schipper et al., *Pharmaceutical Research*, 14(7):923-929 (1997).
Schwarz et al., *British Journal of Rheumatology*, 37(1):21-26 (1998).
Sechriest et al., *J. Biomed. Mater Res*, 49(4):534-541 (2000).
Sellers et al., *The Journal of Bone and Joint Surgery*, 79-A(10):1452-1463 (1997).
Sellers et al., *The Journal of Bone and Joint Surgery*, 82-A(2):151-160 (2000).
Senoo et al., Accession No. 25365 (1990) (abstract).
Shepard et al., *XVIIth FECTS Meeting Patras*, Greece, Abstract Form (Jul. 1-5, 2000).
Shigemasa et al., *Biotechnology and Genetic Engineering Reviews*, 13:383-420 (1995).
Soulhat et al., *Journal of Biomechanical Engineering*, 121:340-347 (1999).
Specchia et al., *Bulletin for Hospital for Joint Diseases*, 54(4):230-235 (1996).
Steadman et al., J. Sports Traumatol. Rel. Res., 20(2):61-70 (1998).
Stone et al., *British Journal of Plastic Surgery*, 53:601-606 (2000).
Suh et al., *Biomaterials*, 21:2589-2597 (2000).
Terbojevich et al., *Carbohydrate Polymers*, 29(1):63-68 (1996).
Ueno et al., *Biomaterials*, 20:1407-1414 (1999).
Van Schie et al., *Diabetes Care*, 23(5):634-638 (2000).
Vasios et al., *45th Annual Meeting*, Orthopaedic Research Society, Anaheim, California, 711 (Feb. 1-4, 1999).
Wakitani et al., *The Journal of Bone and Joint Surgery*, 71-B(1):74-80 (1989).
Wakitani et al., *The Journal of Bone and Joint Surgery*, 76-A(4):579-592 (1994).
Wei et al., *Journal of Biomedical Materials Research*, 34:63-72 (1997).
Yagi et al., *Biol. Pharm. Bull.*, 20(12):1290-1294 (1997).
Zielinski et al., *Biomaterials*, 15(13):1049-1056 (1994).
Zoppou et al., *Bulletin of Mathematical Biology*, 59(5):953-973 (1997).
Ege, S. "Organic Chemistry" 1994.
Hawley's Condensed Chemical Dictionary, 1993, pp. 256.

\* cited by examiner

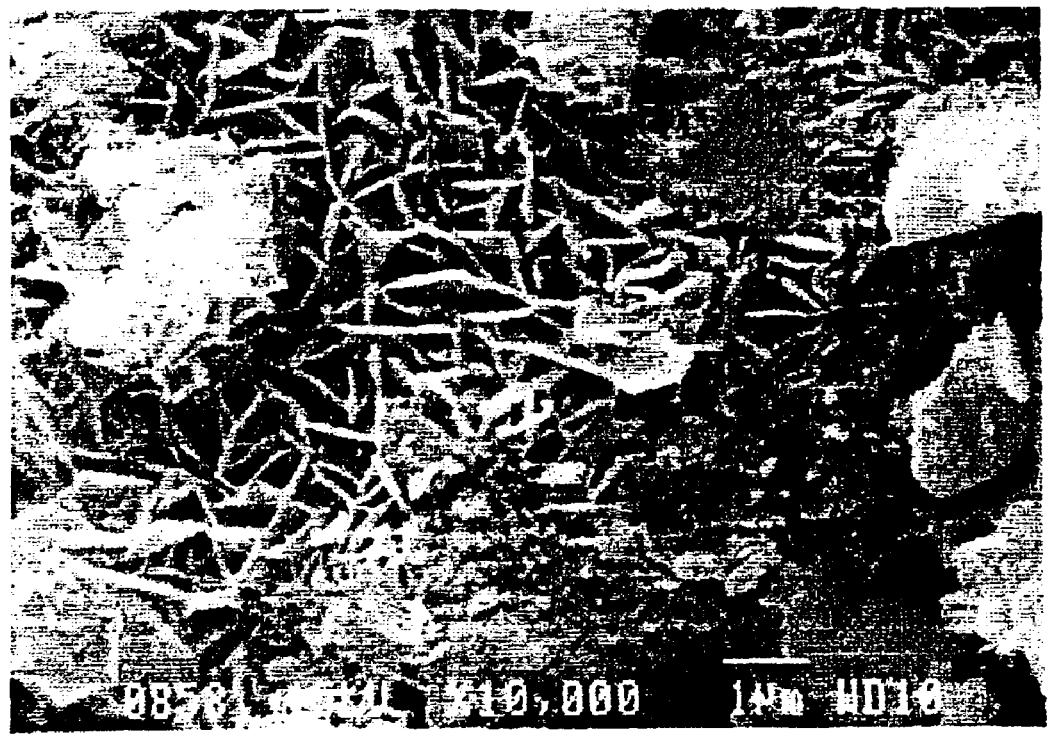
FIG_3

IN SITU SELF-SETTING MINERAL-POLYMER HYBRID MATERIALS, COMPOSITION AND USE THEREOF

BACKGROUND OF THE INVENTION (a) Field of the Invention

The invention relates generally to the preparation and use of an injectable self-setting mineral-polymer composition for repairing, replacing or therapeutically treating tissues and body parts. More particularly, the present invention includes the injectable self-setting mineral-polymer composition.

(b) Description of Prior Art

A large quantity of biomaterials has been introduced for hard-tissue repair and formation, including natural or synthetic materials, pure organic or inorganic materials, and organo-inorganic biohybrid or hybrid materials.

Conductive hard-tissue implants are passive biomaterials that provide a matrix to favor and support a new hard-tissue ingrowth and repair. They generally do not provide any osteogenesis property, in the meaning that such materials do not supply, by themselves, any osteogenesis or hard-tissue inductive factors, or any hard-tissue healing accelerators. Conductive structures have typically to favor the own ingrowth and reorganization of hard-tissues (Ex: osteoconductive materials).

The main constituent of hard-tissues is biological apatite that is commonly found in bone and teeth (65-98%). Calcium and phosphate ions are commonly contained in body fluids and mineral contents of hard tissues, including bones, dentine and dental enamel. They may also additionally contain other constituents such as carbonates, magnesium or sodium. Hydroxyapatite is generally recognized as being a calcium phosphate material with a crystal structure very close to biological apatite. Calcium phosphates, and some other ceramics, were found to be very useful biocompatible materials for hard-tissue repair. Today, a large family of ceramic biomaterials having different forms is available for repairing hard-tissues, and includes calcium phosphates, calcium carbonates, bioglasses and pure natural minerals.

Bone Repair and Formation

Conductive matrices for hard-tissue repair are designed to provide adequate compositions and architectures that favor the ingrowth of hard-tissue by its own. They are inserted into a defect, thus contacting mature hard-tissue cells that are capable of invading the repairing matrix and forming mineral networks to complete tissue ingrowth. Typical examples are generally related to osteoconductive materials for bone tissues.

Conductive hard-tissue implants have received a considerable attention, particularly in bone surgery. Grafting materials for defect filling and bone repair include autografts, xenografts, demineralized bone matrix, porous ceramics such as calcium phosphates, calcium carbonates, coral, nacre, bioglasses, organic matrices (polymers, collagen and other biological macromolecules) as well as organo-inorganic biohybrid or hybrid materials such as organo-apatites.

Implants for filling and repairing defects are currently solids, sometimes gels and hydrogels that enable the ingrowth and conduction of the hard-tissue. Porous or plain solids may be used. Plain solid implants stimulate hard-tissue ingrowth through their own resorption. Porosity may be inherent to the material architecture (true porosity), or be interstitial. Calcium phosphates have been the preferred bone biomaterials. In a large number of animal and human studies, they have been shown to be biocompatible, and bone growth promoters. Targeted calcium phosphate ceramics are tricalcium phosphates, amorphous calcium phosphate, octacalcium phosphate, and apatitic compounds. Hydroxyapatite [$Ca_{10}(PO_4)_6(OH)_2$], calcium-deficient apatite, fluorinated apatite [$Ca_{10}(PO_4)_6F_2$], and carbonated apatite [$Ca_{10-x}H_{ax}(PO_4)_{6-x}(CO_3)_x(OH)_2$] are the most representative apatitic compounds. Synthetic or sintered apatites may be prepared.

Most calcium phosphate ceramics are prepared as granules or block materials. Block materials can be prepared in various geometries such as rods, cylinders, rectangular shapes, etc. However, ceramic blocks must be re-shaped before implantation to fit exactly the defect size and geometry, which makes heavier and longer the handling and clinical application. Furthermore, calcium phosphate blocks are very brittle and difficult to shape, and consequently the interface between the bone tissue and ceramic implant is not perfectly continuous which may impair the osteoconduction efficiency. Calcium phosphate granules are currently produced with a wide size distribution, and available from 10 microns to 2.5 mm, but preferably used with a size between 90 and 400 microns. Granules can be injected, or at least administered through less invasive techniques, so as to fulfill the tissue defect. But granules have a mobility problem in situ, which limits their use and efficiency.

Ceramics such as calcium carbonates, coral or nacre are equally proposed under granular or block form, and present similar problems. Bioglasses are generally under granular or microspheric form (Bioglass®, USBiomaterials; Biogran®, Orthovita; Perioglass®).

Collagen, a component of soft- and hard-tissues, and Bone Demineralized Matrix (BDM) are the current organic materials for filling hard-tissue defects. Collagen was associated with mineral to form composite materials such as Collapat® or Collagraft® (NeuColl), Cerapatite-Collagen® (Ceraver-Osteal), Ossatite® composite (MCP). Polymeric materials such as polylactic acid, polyglycolic acid, polylactic-co-glycolic acid microspheres, etc were also proposed for bone defect filling and repair, but are less current than calcium phosphate granular materials. One new development is Immix® (Osteobiologics) bone-grafting material based on PLA/GA.

Injectable Bone Substitutes

Inorganic or organo-inorganic bone cements and/or remineralizing systems form another family of promising injectable self-setting or self-hardening osteoarticular materials. Self-setting cements were typically composed of a solid mineral component mixed with a liquid component. Solid mineral components generally contain calcium phosphates, such as monocalcium phosphates [$Ca(H_2PO_4)_2.H_2O$], dicalcium phosphates [$CaHPO_4$, $CaHPO_4.2H_2O$], tricalcium phosphates [$\alpha\text{-}Ca_3(PO_4)_2$, $\beta\text{-}Ca_3(PO_4)_2$] and tetracalcium phosphates [$Ca_4(PO_4)O$], with or without other calcium sources and/or phosphate sources, calcium carbonates and/or organic or inorganic additives.

Calcium phosphate remineralizing and cement systems differ by the liquid to solid ratio. Cements are produced from calcium phosphate powder that was finely ground, typically around 5 microns. Calcium phosphate solid component was also mixed with much less liquid, thus forming a paste rather than a slurry. Remineralization was generally promoted by using particles of greater size since they slow the remineralization rate and prolong the remineralization potential.

Porosity of the resulting self-setting calcium phosphate materials may benefit to the hard-tissue repair. It is reached by adding a highly soluble porogen ingredient to the calcium phosphate composition. The composition, including the water-soluble inclusions, is subjected to pressure to form compact materials. Hot water may be used to dissolve the porogenic compound. Others suggested that cement porosity is controlled by the size of dry ingredients. Large-size calcium phosphate granules (0.7-1.0 mm) in the cement composition were found to provide larger pores than small-size granules (0.1-0.3 mm).

Self-setting calcium phosphate composition is transformed following the reaction in situ of calcium phosphate ingredients which is a dissolution/reprecipitation process. The reactivity in situ of calcium phosphates is controlled by chemical and physical conditions. Chemical purity of calcium phosphates may greatly alter the reactivity. Tetracalcium phosphate (TTCP) purity was showed to influence setting and performances of calcium phosphate cements, for example the cement setting time and mechanical strength. TTCP is highly reactive to water, such as air moisture, thus forming calcium oxide or hydroxide, and hydroxyapatite at the TTCP granule surface. Formulation pH and temperature influence the reactivity of calcium phosphates. The size of calcium phosphate particles was also reported to significantly control the reactivity, thus possibly slowing the reaction and retarding the hardening or setting rate when too large. Granule size is related to the exposed surface area, and possibly influences the initial composition of the ingredients, the final dry product composition, and hence the mixing, mechanical and physical properties.

Single calcium phosphate cements cannot set in hard-consistency materials. They were also reported not to be able to maintain a constant pH, and to lack of mineralizing capacity. Driskell et al. (U.S. Pat. No. 3,913,229) described a mixture of tricalcium phosphates and dicalcium phosphate that does not self-harden, and has insufficient remineralizing capacity.

Brown and Chow (U.S. Pat. Nos. 4,612,053; 4,518,430; and Re33,221) proposed a self-setting composition based upon an aqueous mixture of tetracalcium phosphate (TTCP) with at least another calcium phosphate component in excess, selected from dicalcium phosphate or brushite, tricalcium phosphates and modified tricalcium phosphates, octacalcium phosphate [$Ca_8H_2(PO_4)_6 \cdot 5H_2O$] which was able to self-harden into a cement at an ambient temperature. Additional calcium or phosphate sources consisted mainly in $CaCl_2$, $Ca(C_2H_3O_2)$, $NaH_2PO_4$ and $NH_4H_2PO_4$. The slurry containing calcium phosphates in excess had a pH in the vicinity of 7.4. This cement paste was proposed first for dental restorative applications although many orthopedic indications were proposed. Later, Chow and Takagi (U.S. Pat. No. 5,545,254) showed that the preparation of TTCP free of surface calcium oxide or hydroxyapatite greatly improved the quality of such bone cements for dental and orthopedic applications. Remineralization and cement compositions were biocompatible precursors of hydroxyapatite, having two properties: a) they were self-hardening and form materials with sufficient strengths for medical and dental applications; b) they were resorbed in situ and progressively replaced by new hard-tissues.

Liu and Chung (U.S. Pat. No. 5,149,368) proposed other TTCP-based cement formulations where TTCP was admixed with water and acidic citrate to form a paste having a pH greater than 5. The weight ratio of powder to liquid was between 2:1 and 15:1. Constantz et al. (U.S. Pat. No. 5,053,212) developed a composition precursor of hydroxyapatite by admixing a calcium source with an acidic phosphate source. In the preferred embodiment, TTCP was mixed with calcium oxides, calcium carbonates (typically $CaCO_3$), monocalcium phosphate monohydrate (MCPM) and/or orthophosphoric acid. Calcium to phosphate ration was about 1.25-2.0 to 1.0. Later, another bone cement was described where a dry component was admixed with a compatible lubricant and an anti-microbial agent (U.S. Pat. No. 5,968,253). Its dry component was made of reactive α-tricalcium phosphate (60-95% dry wt.), monocalcium phosphate monohydrate (1-20% dry wt.) and calcium carbonate (5-25% dry wt.), and admixed to a phosphate buffer having a pH between 4.0 and 11.0. The anti-microbial agent such as gentamycin or vancomycin was added to the liquid component at 0.001 to 3.0% wt. This flowable composition was the basis of the Norian SRS® bone cement. This composition involved conversion of MCPM into dicalcium phosphate, then formation of hydroxyapatite by reaction of dicalcium phosphate with TTCP. It was setting in approximately 15 minutes, and reached a compression strength about 40 MPa. Another proposed cement composition gave a 2-10% wt. carbonated apatite (U.S. Pat. No. 5,900,254). Dry composition includes a partially neutralized phosphoric acid such as the MCPM and a calcium phosphate source such as the TCP. Calcium carbonate (9-70% dry wt.) was added to the dry component. The liquid component was a 0.01 to 2.0M phosphate buffer, either a sodium phosphate or sodium carbonate, with a pH between 6.0 and 11.0. This composition had the properties of a) having a calcium to phosphate molar ratio of 1.33 to 2.0; b) being not sintered or hydrothermally prepared; and c) having a compression strength above 5500 psi.

Granular bone cements were proposed by admixing a monocalcium phosphate and/or dicalcium phosphates to a α-tricalcium phosphate or a tetracalcium phosphate (U.S. Pat. No. 5,338,356). Calcium to Phosphate ratio was between 1.39 and 1.45, and calcium phosphate granules were 0.1 to 1.0 mm in size. Liquid to Solid ratio varied from 0.3 to 30. Hirano and Hanno (U.S. Pat. No. 5,152,836) also proposed a hydraulic cement made of a mixture of tricalcium phosphates and dicalcium phosphates with a calcium to phosphate ratio between 1.4 and 1.5. Water was used as the hardening liquid component, and water containing soluble sodium was preferred for short hardening times and enhanced cement strengths.

A calcium phosphate cement was proposed and prepared from a TCP/TTCP dry mixture in a liquid component containing calcium and phosphate sources. Liquid component typically contained phosphoric acid, and calcium hydroxide or calcium carbonate. Additives were optionally added to the cement composition, preferably lactic acid (<4% wt.), alginate or gum (<2% wt.), and/or magnesium or potassium glycerophosphate (<15% wt.). Calcium to phosphate ratio of the dry component was about 1.70 to 1.85 while the one of the liquid component was between 0.2 and 0.5. This cement gave a crystalline hydroxyapatite biomaterial with a compressive strength about 15 to 25 MPa.

A calcium orthophosphate composition that hardens in 100% humidity environments into a calcium phosphate cement was composed of a mixture of three to four calcium sources with water. The composition had a pH ranging between 6.5 and 8.0. Calcium sources were selected preferably among monocalcium phosphate monohydrate (MCPM), dicalcium phosphate or brushite, tricalcium phosphates, and modified tricalcium phosphates, octacalcium phosphate, apatites, and other calcium compounds such as $Ca_{8.5}Na_{1.5}(PO_4)_{4.5}(CO_3)_{2.5}$, $Ca_9(PO_4)_{4.5}(CO_3)_{1.5}$, $Ca_4Mg_5(PO_4)_6$, $CaZn_2(PO_4)_2$, $CaKPO_4$, $CaNaPO_4$, $Ca_{10}Na(PO_4)_7$, $Ca_2PO_4Cl$, $CaO$, $Ca(OH)_2$, $CaMgO_2$ and $Ca_{10}(PO_4)_6Cl_2$.

Basic calcium phosphate cements self-setting in hydroxyapatite were developed by Chow and Takagi (U.S. Pat. Nos. 5,525,148 and 5,954,867). Liquid components contained liquid phosphate component having a pH above 12.5 (phosphate >0.2 mol/l). Solid calcium phosphate component had a Calcium to Phosphate between 3.0 and 5.0, included various calcium phosphates, except TTCP, and a calcium source.

Proposed calcium phosphates were dicalcium phosphates, tricalcium phosphates, octacalcium phosphate and/or amorphous calcium phosphate. Additional sources of calcium were selected typically among calcium carbonates, calcium oxides, and calcium hydroxides. Additional minerals were also added in minor concentrations. The pH of the composition was potentially adjusted above 12.5 by adding sodium hydroxide.

Commercial developments in calcium phosphate bone cements are given by SRS® (Norian), BoneSource® (Stryker/Howmedica), alpha-BSM® (ETEX Corp.), all three giving carbonated apatite in situ, and Cementek® (Teknimed SA).

Most common calcium phosphates in self-setting cements were selected from monocalcium phosphate monohydrate $[Ca(H_2PO_4)2.H_2O]$, dicalcium phosphate (DCP) or brushite $[CaHPO_4, CaHPO_4.2H_2O]$, tricalcium phosphate (TCP) $[\alpha-Ca_3(PO_4)_2, \beta-Ca_3(PO_4)_2]$, tetracalcium phosphate (TTCP)$[Ca_4(PO_4)O]$, amorphous calcium phosphate (ACP) $[Ca_3(PO_4)2.H_2O]$, octacalcium phosphate (OCP) $[Ca_8H_2(PO_4)_6. 5H_2O]$, and apatites $[Ca_{10}(PO_4)_6(OH)_2]$.

All calcium phosphates have different dissolution rate at a given pH. For a calcium to phosphate molar ratio above 1.5, the dissolution rate can be defined (at least up to a pH about 10) as follows: Tetracalcium phosphate>$\alpha$-tricalcium phosphate>$\beta$-tricalcium phosphate>hydroxyapatite.

Calcium phosphates have also a relative acidic or basic character, thus increasing acidity or basicity.

Acidic components generally include, in an acidity order: monocalcium phosphate monohydrate>dicalcium phosphate>octacalcium phosphate>amorphous calcium phosphate=$\beta$-tricalcium phosphate=$\alpha$-tricalcium phosphate=calcium-deficient apatite. Monocalcium phosphate monohydrate is generally used as acidic calcium phosphate source when necessary.

Basic calcium phosphates generally include, in a basicity order: tetracalcium phosphate>precipitated hydroxyapatite=sintered hydroxyapatite>$\alpha$-tricalcium phosphate=calcium-deficient apatite=$\beta$-tricalcium phosphate=amorphous calcium phosphate. Calcium sources such as calcium oxides and hydroxides are more basic than tetracalcium phosphate.

Exothermic setting reactions may be damageable to living tissues and cells in situ. High temperatures generated by the cement setting being undesirable, it is thus desirable to keep the setting temperature well below 50-60° C. Exothermic effects in calcium phosphate cements are typically obtained by reacting calcium oxides with acidic phosphate sources. The transformation of calcium oxide into calcium hydroxide is recognized to be exothermic. Pressure level of cement composition may also change during the setting reaction. Calcium carbonate [$CaCO_3$] is for neutralizing and buffering the formulation, but generates carbon dioxide gas. In situ formation of carbon dioxide gas is susceptible of pressure elevation, and may induce unexpected structural modifications or changes of the resulting material. Calcium carbonate, and other carbonates, in cement composition must be specially considered for this gas supply and pressure increase in situ.

Incorporation of polymer in cement composition was proposed to give some specific properties: a) to improve the handling properties and wettability of the cement; b) to avoid the cement composition to disintegrate in aqueous media such as the physiological fluids, and allow to pre-shape the composition; as a consequence, this reduced the need for removal of body fluid, hemostasis, or the like.

Polyacid or polyol polymers, polysaccharides and polypetidics were preferentially chosen for incorporation in calcium phosphate cement compositions. Polycarboxylics (polycarboxylic acid), poly(ethylene glycol), poly(propylene glycol), methyl cellulose, poly(vinyl alcohol), carboxymethyl cellulose, hydroxypropyl methylcellulose, and the like, were proposed as polymeric components. Collagen was optionally introduced in a cement composition by Constantz et al. (U.S. Pat. No. 5,053,212). Chitin, chitosan, starch, gum, pectic acid, alginic acid, hyaluronic acid, chondroitin sulfuric acid, dextran sulfuric acid and their salts were reported as potent polysaccharide ingredient (U.S. Pat. Nos. 5,152,836; and 5,980,625; and European patent application publication No. EP-899,247 A1).

Chitosan was admixed in many liquid components of calcium phosphate cement compositions. Chitosan in citric, malic, or phosphoric acid aqueous medium was the liquid component of a self-setting TCP or TCP/TTCP cement (U.S. Pat. Nos. 5,281,404 and 5,180,426). Chitosan in bone cements or substitutes was also studied in the scientific literature, as reported by Leroux et al. (*Bone*, Vol. 25, No 2, supplement, 1999:31S-34S), Hidaka et al. (*J. Biomed. Mat. Res.*, 46:418-423, 1999), Ito (*Biomaterials*, 12:41-45, 1991). It has also been reported the use of chitosan in calcium phosphate compositions. Typically, chitosan 0.05% wt. in an acidic aqueous medium (acid 25-55% wt.) was used as lubricant for a solid component consisting in a mixture of TCP and TTCP. Chitosan was chosen to prevent the powder dispersion and cement disintegration.

Osteoconduction and osteogenic performances of chitosan based materials were reviewed, and applied to biomaterials development. Chitosan with immobilized polysaccharides such as heparin, heparan sulfate, chondroitin sulfate and dextran sulfate was reported for stimulating hard-tissue regeneration by Hansson et al. (International Patent Application publication WO96/02259). Osteoinductive compositions were also developed by admixing hydroxyapatite and bone-derived osteoinductive gelatin to chitosan solutions (U.S. Pat. No. 5,618,339).

It would be highly desirable to be provided with a self-hardening mineral polymer hybrid composition with attractive performance for biomedical uses.

It would also be highly desirable to be provided with a gel-forming liquid component that enables to enhance the handling and cohesion properties of a new self-hardening material.

It would still be highly desirable to be provided with a liquid component that contains a chitosan solution, free of insoluble particle, with a pH close to 7.0 and a thermo-gelling character. This would be innovative and allow developing an in-situ self-hardening material based upon a mineral composition.

SUMMARY OF THE INVENTION

One aim of the present invention is to provide a self-setting mineral-polymer composition that can be applied to defects or cavities of hard-tissues, or to an anatomical structure of hard-tissues, or a body cavity, thus enabling the formation in situ of a group of bio-materials having distinct compositions, functions and properties.

In accordance with the present invention there is provided a new injectable in situ self-setting mineral-polymer composition that can be conveniently used for hard-tissue repair, replacement or treatment in mammalians or humans.

Also in accordance with the present invention, there is provided an injectable self-setting composition comprising:

a) a water-based liquid component comprising at least one cationic polymer and one mono-phosphate salt; said liquid component having a pH ranging from 6.5 to 7.4, said liquid component having an endothermally gelling character and being free of insoluble particles; and b) a powder component comprising at least two calcium phosphate sources selected from apatites and apatitic calcium phosphates, octacalcium phosphates, amorphous calcium phosphates, tetracalcium phosphates, tricalcium phosphates, dicalcium phosphates and monocalcium phosphates, wherein when said components of step a) and b) are intimately and uniformly mixed together, said components of step a) and b) form an injectable thermo-setting slurry, said slurry when heated turns into a solid material.

The cationic polymer may be a polysaccharide, a polypeptide or a synthetic polymer. The cationic polymer may have a concentration in said liquid component between 0.1 and 5.0% wt. The cationic polymer is preferably chitosan or collagen, or a mixture of chitosan and collagen. The cationic polymer can also be a partially-deacetylated chitin or chitosan with a degree of deacetylation between 30 and 99%. The cationic polymer can further be a polylysine.

The monophosphate salt may have a basic character.

The liquid component can comprise a first phosphate source selected from the group consisting of $Na_2PO_4C_3H_5(OH)_2$, $Fe_2PO_4C_3H_5(OH)_2$, $K_2PO_4C_3H_5(OH)_2$, $MgPO_4C_3H_5(OH)_2$, $MnPO_4C_3H_5(OH)_2$, $Ca_2PO_4C_3H_5(OH)_2$, $Na_2PO_7C_3H_7$, $Na_2PO_7C_4H_7$, $K_2PO_7C_4H_7$, $NaPO_7C_4H_8$, $K_2PO_7C_4H_8$, $Na_2PO_8C_5H_9$, $K_2PO_8C_5H_9$, $NaPO_8C_5H_{10}$, $KP0_8C_5H_{10}$, $Na_2PO_9C_6H_{11}$, $NaPO_9C_6H_{12}$, $K_2PO_9C_6H_{11}$, $KPO_9C_6H_{12}$, $Na_2PO_8C_6H_{13}$, $K_2PO_8C_6H_{13}$, $NaPO_8C_6H_{14}$, $KPO_8C_6H_{14}$, $Na_2PO_9C_6H_{12}$, $K_2PO_9C_6H_{12}$, $NaPO_9C_6H_{13}$, $KPO_9C_6H_{13}$, $Na_2PO_8C_{10}H_{11}$, $K_2PO_8C_{10}H_{11}$, $NaPO_8C_{10}H_{12}$, $KPO_8C_{10}H_{12}$ and the like, or a derivative thereof.

The monophosphate salt is a sodium, magnesium, potassium, ferric and/or calcium alpha- or beta-glycerophosphate salt, or a mixture thereof.

The monophosphate salt may be glucose-1-phosphate, glucose-6-phosphate, fructose-1-phosphate or fructose-6-phosphate salt, or a mixture thereof.

The liquid component preferably has a pH between 6.8 and 7.2 and a viscosity superior to 200 mPa·s.

The liquid component can further comprise at least one other water-soluble polymer selected from the group consisting of polypeptides, cellulosics and synthetic polymers, including methyl cellulose, hydroxyethyl cellulose, hydroxypropyl cellulose, hydroxyethyl propylcellulose, hydroxymethyl propylcellulose, poly(ethylene oxide), poly(propylene oxide), poly(ethylene glycol), poly(vinylpyrrolidone), poly(vinyl alcohol), and derivatives thereof.

The liquid component can also further comprise at least one organic polyol, including sugar-polyol, saccharide-polyol and glycol, selected from the group consisting of glycerol, mannitol, sorbitol, ethylene glycol oligomers, propylene glycol oligomers, saccharose, fructose, glucose, maltose, and the like.

The liquid component can further comprise at least one water-soluble amino acid having a basic character and a pKa between 6.5 and 8.5, or alternatively the liquid component can further comprise a water-soluble sulfonate or carboxylate salt having a basic character and a pKa between 6.5 and 8.5.

The liquid component and the powder component preferably have a ratio liquid/powder component from 0.05 to 1.50 mL/g.

The composition preferably has a final molar ratio of calcium/phosphorus between 1.20 and 1.80.

The powder component can comprise alpha-tricalcium phosphate and an apatitic calcium phosphate, or alpha-tricalcium phosphate, dicalcium phosphate and an apatitic calcium phosphate.

The powder component can comprise alpha-tricalcium, monocalcium phosphate and an apatitic calcium phosphate.

The powder component can comprise at least alpha-tricalcium phosphate and an amorphous calcium phosphate.

The powder component can comprise tetracalcium phosphate and dicalcium phosphate, or tetracalcium phosphate and monocalcium phosphate. Preferably, the powder component comprises less than 40% wt. of an apatitic calcium phosphate.

The powder component can further comprise at least one fluoride selected from the group consisting of NaF, $Na_2Si_6F$, KF, $KSi_6F$, $CaF_2$, $MgF_2$, $ZnF_2$, and sodium fluorophosphates, and the like, or derivatives thereof.

The powder component can further comprise at least one carbonate selected from the group consisting of $Na_2CO_3$, $CaCO_3$, $K_2CO_3$, $MgCO_3$, $ZnCO_3$, $Ca_9K(PO_4)_5(CO_3)_2$, $Ca_{8.5}Na_{1.5}(PO_4)_{4.5}(CO_3)_{2.5}$, $Ca_9(PO_4)_{4.5}(CO_3)_{1.5}$, and the like.

The powder component preferably comprises a strontium salt including strontium carbonate or at least one calcium phosphate selected from the group consisting of fluoride, strontium, carbonate, magnesium, zinc, and barium containing calcium phosphates.

The powder component can comprise at least one inorganic salt including sodium phosphates and disodium glycerophosphate, or the like, or alternatively, it can comprise at least one organic salt including oxalate, citrate, malate, gluconate, lactate, lactobionate, or the like.

The powder component can comprise at least one organic salt including oxalic, citric, malic, gluconic, lactic, lactobionic acids, or the like.

The powder component is preferably a powder having a size ranging from 0.1 to 100 micrometers.

Preferably, the composition further comprises a bioactive ingredient such as a drug, a protein, a peptide, a synthetic molecule or an inorganic molecule, or it can comprise at least one osteoinductive agent selected from the group consisting of hormones, bone proteins and mixtures of osteoinductive proteins, demineralized bone matrix (DBM) or powder (DBP), bone morphogenic proteins (BMP), sialoproteins, osteonectin, osteopontin, osteocalcin, calcitonin. Preferably, the composition further comprises at least one growth factor selected from the group consisting of IGF, EGF, a-FGF, b-FGF, PDGF-A, PDGF-B and TGF-beta.

The composition can also further comprise an antiresorptive, antibiotic, antiviral, antitumor, or an immunosupressive agent.

In accordance with the present invention, there is also provided the use of the composition as defined above for injection into a defect, cavity or interface of a body's tissue, said composition setting in situ into a hardened filling material, or for the manufacture of a medicament for injection. The composition may be injected into a defect, cavity or interface of a cancellous, cortical or corticocancellous bone. The composition may also be injected into the metaphysis or diaphysis of a bone or into a fractured bone, between the bone fragments of fractured bone. The composition once injected sets in situ into a filling hardened material.

Further in accordance with the present invention, there is also provided an injectable self-setting composition comprising:

c) a liquid component, free of insoluble material, comprising, an organic and/or inorganic acid, a partially N-deacetylated chitosan and/or a collagen, and a glycerophosphate; said liquid component having a pH ranging from 6.5 to 7.4, said liquid component having an endothermally gelling character, said partially N-deacetylated chitosan having a final concentration ranging between 0.5 to 3.0% w/v, and said glycerophosphate salt having a final concentration ranging between 1.0 to 10.0% w/v, and d) a powder component comprising a dry mixture of a tricalcium phosphate with a calcium deficient apatite or an octacalcium phosphate, and with at least one of an inorganic salt, an organic salt, an organic acid source and an organic compound, wherein when said components of step a) and b) are intimately and uniformly mixed together, said components of step a) and b) form an injectable thermo-setting slurry, said slurry when heated turns into a solid material.

Still in accordance with the present invention, there is provided an injectable self-setting composition comprising:

a) a liquid component, free of insoluble particle, comprising an organic and/or inorganic acid, a partially N-deacetylated chitosan and/or a collagen, and a glycerophosphate; said liquid component having a pH ranging from 6.5 to 7.4, said liquid component having an endothermally gelling character, said partially N-deacetylated chitosan has a concentration ranging between 0.5 to 3.0% w/v, and said glycerophosphate salt has a concentration ranging between 1.0 to 10.0% w/v, and b) a powder component comprising a dry mixture of a tetracalcium phosphate with a calcium deficient apatite or an octacalcium phosphate, and with at least one of an inorganic salt, an organic salt, an organic acid source and an organic compound, wherein when said components of step a) and b) are intimately and uniformly mixed together, said components of step a) and b) form an injectable thermo-setting slurry, said slurry once heated setting into a solid material.

Preferably, the inorganic salt is selected from carbonate, phosphate, strontium, fluoride salts, and the like, and the organic salt is preferably selected from citrate, malate, lactate, gluconate salts, and the like.

The organic acid can be selected from citric acid, malic acid, lactic acid, gluconic acid, and the like, and the organic compound can be selected from the group consisting of biological fluids and components, water-soluble or miscible organic polyols, drugs, amino-acids, proteins, and the like.

The composition can also further comprise a water-soluble or miscible organic polyol, including sugar-polyol, saccharide-polyol and glycol, selected from the group consisting of glycerol, mannitol, sorbitol, ethylene glycol oligomers, propylene glycol oligomers, saccharose, fructose, glucose, maltose, and the like.

The composition can still comprise glucosamine and/or histidine.

The composition can further comprise a strontium containing compound, a carbonate containing compound or a fluoride containing compound.

Also in accordance with the present invention, there is provided a method of preparation of an injectable self-setting composition, said method comprising the step of admixing a water-based liquid component comprising at least one cationic polymer and one mono-phosphate salt with a powder component comprising at least two calcium phosphate sources selected from apatites and apatitic calcium phosphates, octacalcium phosphates, amorphous calcium phosphates, tetracalcium phosphates, tricalcium phosphates, dicalcium phosphates and monocalcium phosphates, wherein said liquid component comprising at least one cationic polymer and one mono-phosphate salt; said liquid component having a pH ranging from 6.5 to 7.4, said liquid component having an endothermally gelling character and being free of insoluble particles, said admixing thus forming an injectable thermo-setting slurry, said slurry when heated turns into a solid material.

In one embodiment of the invention, there is provided a method of preparation of an injectable self-setting composition, said method comprising admixing a liquid component, free of insoluble material, comprising, an organic and/or inorganic acid, a partially N-deacetylated chitosan and/or a collagen, and a glycerophosphate, with a powder component comprising a dry mixture of a tricalcium phosphate with a calcium deficient apatite or an octacalcium phosphate, and with at least one of an inorganic salt, an organic salt, an organic acid source and an organic compound, said liquid component having a pH ranging from 6.5 to 7.4, said liquid component having an endothermally gelling character, said partially N-deacetylated chitosan having a final concentration ranging between 0.5 to 3.0% w/v, and said glycerophosphate salt having a final concentration ranging between 1.0 to 10.0% w/v, said admixing thus forming an injectable thermo-setting slurry, said slurry when heated turns into a solid material.

In a further embodiment of the invention, there is also provided a method of preparation of an injectable self-setting composition, said method comprising admixing a liquid component, free of insoluble particle, comprising an organic and/or inorganic acid, a partially N-deacetylated chitosan and/or a collagen, and a glycerophosphate with a powder component comprising a dry mixture of a tetracalcium phosphate with a calcium deficient apatite or an octacalcium phosphate, and with at least one of an inorganic salt, an organic salt, an organic acid source and an organic compound, said liquid component having a pH ranging from 6.5 to 7.4, said liquid component having an endothermally gelling character, said partially N-deacetylated chitosan has a concentration ranging between 0.5 to 3.0% w/v, and said glycerophosphate salt has a concentration ranging between 1.0 to 10.0% w/v, said admixing thus forming an injectable thermo-setting slurry, said slurry when heated turns into a solid material.

For the purpose of the present invention the following terms are defined below.

In the present invention, the term "endothermally sensitive" solution refers herein to a solution turning into a gel material with an increasing temperature. In that meaning, endothermally sensitive may be easily replaced by "endothermally gelling" and "thermo-gelling".

In accordance with the present invention, the composition comprises a liquid component and a solid component, such components being intimately mixed together; said liquid component being endothermally sensitive as previously defined.

The term "mineral-polymer hybrid" refers herein to a biphasic system where a mineral component is associated to a polymer component, whatever said mineral and polymer components are liquid or solid.

The term "liquid component (or phase)" refers herein to the component that is a water-based solution, and particularly a water-based polymeric solution.

The term "powder component (or phase)" refers herein to the component that is a solid material, said solid materials being preferably a powder, particulate or granular material. Also used for solid component is "mineral component or phase".

The term "dry ingredient" refers to a dry solid material that enters in the preparation of the solid component and mineral-polymer hybrid composition. In most cases, it is a mixture of solid particulates made of minerals or organics.

"Apatitic" refers herein to a compound that has mainly an apatite-related crystallographic phase.

"Bioactive agent" refers herein to a substance that presents an established biological activity of interest for the use of the hybrid composition. "Non-bioactive agent" corresponds to a substance used without any consideration for a possible biological activity of the hybrid composition.

"Self-setting" refers herein to a reaction that occurs in the hybrid composition between the components of the liquid and solid components. It is basically a dissolution and reprecipitation of the minerals of the solid component in the liquid component. It results in macroscopic and characteristics changes of the hybrid composition.

"Self-hardening" refers herein to the formation of a continuous solid material or network within the hybrid composition. This material or network is built from minerals, but may incorporate organic (mineral-polymer). Self-hardening excludes self-gelling. Self-hardened materials are not highly hydrated, and do not correspond to gels.

"Self-gelling" refers herein to the sol-gel transition associated to the liquid component, resulting in the formation of uniform three-dimensional hydrated network (mainly organic). The self-gelling reaction is a reaction intrinsic to the polymer in the liquid component. Herein, gelling exclude hardening.

"Gel-like" refers to a material that has the appearance of a homogeneous highly hydrated gel.

In the present invention, the new in situ self-setting mineral-polymer composition refers specially to a composition and bio-material, described by an injectable self-forming hard-tissue composition and substitute wherein the material formation in situ is related to solid-like materials; said compositions and substitutes are defined herein by "self-setting (self-hardening) mineral-polymer hybrid compositions, bio-materials" or "self-setting cement-like materials".

BRIEF DESCRIPTION OF THE DRAWINGS

FIG. 3 illustrates micro-structural view (scanning electron microscopy) of self-setting mineral-polymer hybrid materials with apatite crystals;

DETAILED DESCRIPTION OF THE INVENTION

Figure 1:
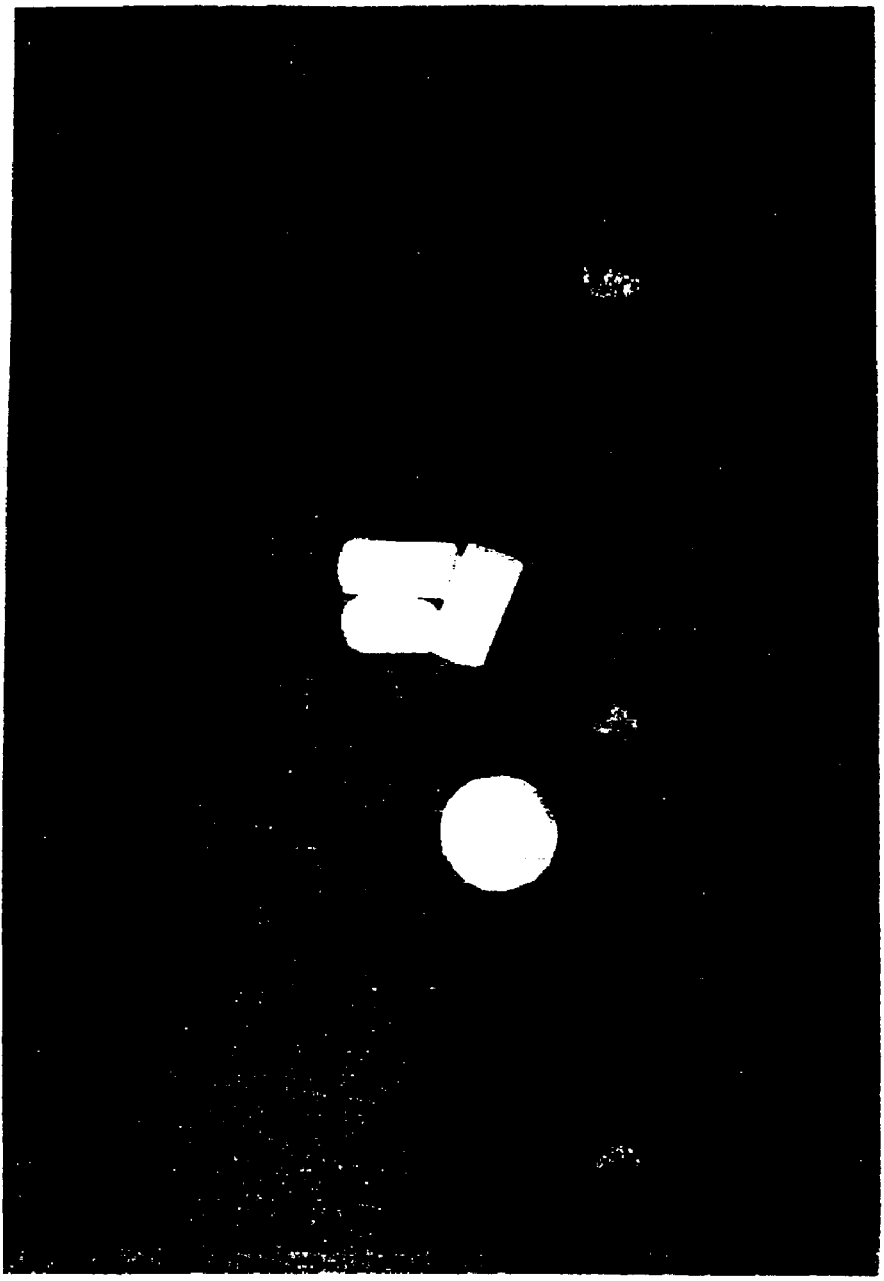
FIG. 1 illustrates a general view of self-setting mineral-polymer hybrid materials in accordance with the present invention, after setting in vitro, wherein hybrid materials have been shaped prior to self-setting at 37° C. in a moist environment.

In one embodiment, a self-setting mineral-polymer composition comprises a thermo-gelling liquid component and a mineral powder component that gives a self-setting (self-hardening) composition at the body temperature. Various composition of the present invention can be self-hardening to various levels, which give potent high strengths, mainly ceramic-composed, solid bio-materials with a plain or porous structure.

The composition of the present invention is preferably used with hard-tissues of the body, typically bone, dentine and enamel.

Preparation of the Liquid Component

In the present invention, the liquid component is an endo-thermally sensitive solution, and consists in a polymeric aqueous solution. In a preferred embodiment, the liquid component comprises water, and an acid-soluble organic and/or inorganic acid, at least one acid-soluble cationic polymer, and at least one water-soluble phosphate source. In other embodiments, the composition comprises water, and an acid-soluble organic and/or inorganic acid, at least one acid-soluble cationic polymer, at least one of a water-soluble phosphate, and one of water-soluble sulfonate and carboxylate salt. The acid-soluble cationic polymer is defined as being a hydrophilic cationic polymer that is soluble in an acidic aqueous medium with a pH inferior to 6.5.

The liquid component is characterized by its endothermal sensitivity which means generally that it presents a sol-gel transition temperature (SGTT), a liquid state (sol state) at a temperature lower than the SGTT, and a gel state comprising a gel which is substantially water-insoluble at a temperature higher than the SGTT.

In the liquid component, the acid-soluble polymer is dissolved by using organic and/or inorganic acids, including malic acid, propionic acid, phosphoric acid, glycerophosphoric acid, orthophosphoric acid, lactic acid, hydrochloric acid, ascorbic acid, formic acid, acetic acid, and the like. The polymer is dissolved in an acidic aqueous medium having a pH ranging between 1.0 and 5.0, preferentially between 1.0 and 4.0. The acid-soluble cationic polymer is a hydrophilic polysaccharide, including partially deacetylated chitins and chitosans, and an amino-substituted polysaccharide having the desired properties. It can also be an amino-substituted dextran. The acid-soluble cationic polymer can also be a polypeptidic or poly(amino acids) including collagens and polylysine, and a synthetic cationic polymer including polyacrylamide, and the like. The content in the acid-soluble polymer is ranging between 0.1% and 10% w/v, preferentially between 0.5 and 5.0% w/v, and more preferably between 0.5% and 3.0% w/v.

The cationic polymer may be optionally combined with another polymer selected from polysaccharides, polypeptides, cellulosics and synthetic polymers, including modified chitin, modified chitosans, collagen, methylcellulose, hydroxyethyl cellulose, hydroxypropyl cellulose, hydroxyethylpropyl cellulose, hydroxymethyl propylcellulose, poly (ethylene oxide), poly(ethylene glycol), poly(propylene oxide), poly(vinyl alcohol), poly(vinyl pyrrolidone), and the like, or a mixture thereof. The content in this other polymer varies between 0.01% and 5.0% w/v, preferentially between 0.01% and 2.5% w/v, and more preferably between 0.01% and 1.0% w/v. A typical example of other polymer is a N,O-carboxymethylchitosan or a N,O-glycolic-chitosan or N,O-lactic-chitosan, a poly(ethylene oxide), poly(ethylene oxide-co-propylene oxide-co-ethylene oxide), or methyl cellulose. In one embodiment, a preferred other polymer is a collagen solubilized at a concentration between 0.5 to 10% w/v.

In one embodiment, the water-soluble phosphate source of the liquid component is defined as being an organic mono-phosphate basic salt. It has a moderate basic character, and a pKa between 6.0 and 7.4. This phosphate source is preferentially a (di)sodium, (di)potassium, magnesium, manganese or (di)ferric salt, and more preferably a disodium, dipotassium or magnesium salt, or a mixture thereof. The concentration of the phosphate source of the liquid component is between 0.1% and 20% w/v, and ideally between 0.5% and 10% w/v. The phosphate source is preferably selected in a group comprising $Na_2PO_4C_3H_5(OH)_2$, $Fe_2PO_4C_3H_5(OH)_2$, $K_2PO_4C_3H_5(OH)_2$, $MgPO_4C_3H_5(OH)_2$, $MnPO_4C_3H_5(OH)_2$, $Ca_2PO_4C_3H_5(OH)_2$, $Na_2PO_7C_3H_7$, $Na_2PO_7C_4H_7$, $K_2PO_7C_4H_7$, $NaPO_7C_4H_8$, $K_2PO_7C_4H_8$, $Na_2PO_8C_5H_9$, $K_2PO_8C_5H_9$, $NaPO_8C_5H_{10}$, $KPO_8C_5H_{10}$, $Na_2PO_9C_6H_{11}$, $NaPO_9C_6H_{12}$, $K_2PO_9C_6H_{11}$, $KPO_9C_6H_{12}$, $Na_2PO_8C_6H_{13}$, $K_2PO_8C_6H_{13}$, $NaPO_8C_6H_{14}$, $KPO_8C_6H_{14}$, $Na_2PO_9C_6H_{12}$, $K_2PO_9C_6H_{12}$, $NaPO_9C_6H_{13}$, $KPO_9C_6H_{13}$, $Na_2PO_8C_{10}H_{11}$, $K_2PO_8C_{10}H_{11}$, $NaPO_8C_{10}H_{12}$, $KPO_8C_{10}H_{12}$, and the like, and derivatives thereof or a mixture thereof. Ideally, the phosphate source is alpha- or beta-glycerophosphate (glycerol-2-phosphate, glycerol-2-phosphate), glucose-1-phosphate, glucose-6-phosphate, fructose-1-phosphate or fructose-6-phosphate disodium or dipotassium, magnesium, or a mixture thereof.

The liquid component may optionally comprise at least one sulfonate source, in a proportion of 0.1 to 10% w/v, selected among N-[carbamoylmethyl]-2-aminoethane sulfonate (ACES), N,N-bis[2-hydroxyethyl]-2-aminoethane sulfonate (BES), 3-[N,N-bis(2-hydroxyethyl)amino]-2-hydroxy propanesulfonate (DIPSO), N-[2-hydroxyethyl]piperazine-N'-3-propane-sulfonate (EPPS), N-[2-hydroxyethyl]piperazine-N'-3-propanesulfonate (HEPES), 2-[N-morpholino]ethanesulfonate (MES), 4-[N-morpholino]butane-sulfonate (MOBS), N-tris[hydroxymethyl]methyl-2-minoethane-sulfonate (TES), and the like, or a mixture thereof.

The liquid component may optionally comprise other molecules such as water-soluble molecules having one acid and at least two amino groups, or more amino groups than acid groups, or at least one amino groups and multiple alcohol groups; said molecules having a moderate basic character and a pKa between 6.0 and 7.4. This molecule is generally selected among amino-acid residues or sequences, including histidine (HIS) or lysine (LYS) residues or sequences, and/or among a group comprising bis[2-hydroxyethyl]iminotris[hydroxymethyl]methane (BIS-TRIS), Tris[hydroxy-methyl] amino-methane (TRIZMA), and the like, or a mixture thereof.

All proposed liquid components have a pH ranging between 6.5 and 7.4, an intrinsic viscosity ranging between 5 and 100,000 mPa·s at 21° C. All liquid components, being endothermally sensitive, have a sol-gel transition temperature, and form homogeneous solid aqueous gels at a temperature, between 15° C. and 60° C., preferably between 25° C. and 45° C., and more preferably at 35-40° C.

Other organic compounds being non-bioactive may be admixed to the liquid component so as to provide specific chemical or physical properties. Representative compounds include sugar-polyols such as glycerol, mannitol or sorbitol, and saccharide-polyols such as fructose, glucose, lactose or maltose, and glycols such as ethylene glycol oligomers, propylene glycol oligomers, and the like. Sugar-polyols, saccharide-polyols and glycols may be incorporated alone or in combination. The final concentration of sugar-polyols, saccharide-polyols and glycols in the liquid component is typically below 20% wt., preferably between 1.0 and 15.0% wt.

Other water-soluble salt may be added to the liquid component as required and permitted by the thermo-gelling property. This includes water-soluble fluoride, phosphate and carbonate salts, generally at a concentration below 0.1 mol/l.

In one embodiment, the liquid component is composed of chitosan and disodium glycerophosphate, has a pH above the pKa of chitosan (6.3-6.4), generally between 6.5 and 7.4, and a reduced content in acid. Typically, chitosan-glycerophosphate solutions at pH=7.0, prepared from chitosan, hydrochloric acid and disodium glycerol-phosphate, mainly contain water, chitosan-glycerophophate and NaCl.

Preparation of the Powder Component

In the invention, the solid component is a mixture of dry mineral powders or particles, also called "dry ingredients". The size of the particles is not particularly crucial in the invention, although there exist preferred ranges of sizes to have optimal particle surface area, surface reactivity, dissolution rate, etc. The dry ingredient of the present invention comprises at least two calcium phosphates, but optionally comprises also a calcium source, a sodium phosphate, other minerals and organics.

The solid component consists in a dry powder mixture that comprises at least two calcium phosphate sources. The two calcium phosphate sources are selected among apatitic calcium phosphates, octacalcium phosphates, amorphous calcium phosphates, tetracalcium phosphates, tricalcium phosphates, dicalcium phosphates and monocalcium phosphates. Apatites comprise sintered hydroxyapatite $Ca_{10}(PO_4)_6(OH)_{2-2x}O_x$ (SHA, Ca/P=1.67), precipitated hydroxyapatite $Ca_{10}(PO_4)_6(OH)_2$ (PHA, Ca/P=1.67), all calcium-deficient apatites such as the apatite of formula $Ca_9(HPO_4)(PO_4)_5OH$ (CDA, Ca/P=1.5), and the like, and derivatives thereof. Calcium deficient apatites are apatitic calcium phosphates with Ca/P molar ratio in the range 1.66 to 1.5 or less. Compounds including interlayers of octacalcium phosphate are included.

The calcium phosphates can be selected in a group comprising $Ca(H_2PO_4)_2 \cdot H_2O$, $CaHPO_4 \cdot 2H_2O$, $CaHPO_4$, $CaZn_3(PO_4)_2$, $CaZnPO_4$, $CaNaPO_4$, $Ca_2PO_4Cl$, alpha-$Ca_3(PO_4)_2$, beta-$Ca_3(PO_4)_2$, $Ca_3(PO_4)_2 \cdot H_2O$, $Ca_4(PO_4)_2O$, $Ca_8H_2(PO_4)_6 \cdot 5H_2O$, $Ca_9(HPO_4)(PO_4)_5OH$, $Ca_{10}(PO_4)_6(OH)_{2-2x}O_x$, $Ca_{10}(PO_4)_6(OH)_2$, and derivatives thereof. Calcium phosphate sources may comprise natural mineral components including hard-tissue, enamel or dental apatite, coral or nacre. Calcium phosphate sources may also be selected among apatitic and nonapatitic calcium phosphates containing fluoride, strontium or carbonate (calcium fluoride phosphates, calcium strontium phosphates, carbonated calcium phosphates, fluorinated and carbonated calcium phosphates, fluorinated calcium strontium phosphates, fluorinated and carbonated calcium strontium phosphates, and the like).

The solid component may also comprise a phosphate source such as a sodium phosphate compound.

The solid component may also comprise a calcium source selected in a group comprising CaO, $Ca(OH)_2$, $CaCO_3$, $CaCl_2$, $CaMgO_2$, $CaF_2$, $CaPO_4C_3H_5(OH)_2$, $Ca(H_2PO_4)_2 \cdot H_2O$, $CaHPO_4 \cdot 2H_2O$, $CaHPO_4$, alpha-$Ca_3(PO_4)_2$, beta-$Ca_3(PO_4)_2$, $Ca_3(PO_4)_2 \cdot H_2O$, $Ca_4(PO_4)_2O$, $Ca_8H_2(PO_4)_6 \cdot 5H_2O$, $Ca_9(HPO_4)(PO_4)_5OH$, $Ca_4Mg_5(PO_4)_6CaO$, $Ca_{10}(PO_4)_6Cl_2$, $Ca_{10}(PO_4)_6(OH)_{2-2x}O_x$, $Ca_{10}(PO_4)_6(OH)_2$, and derivatives thereof.

The solid component may comprise other mineral ingredients such as a carbonate, strontium, fluoride, magnesium, zinc or barium source, or other minerals. Carbonates may be typically selected among $Na_2CO_3$, $CaCO_3$, $K_2CO_3$, $MgCO_3$, $ZnCO_3$, $Ca_9K(PO_4)_5(CO_3)_2$, $Ca_{8.5}Na_{1.5}(PO_4)_{4.5}(CO_3)_{2.5}$, $Ca_9(PO_4)_{4.5}(CO_3)_{1.5}$, and the like. The fluoride source may be selected among NaF, $Na_2Si_6F$, KF, $KSi_6F$, $CaF_2$, $MgF_2$, $ZnF_2$, and the like. Strontium compounds may be strontium salts (strontium chloride, oxides and the like), strontium phosphate salts. Other ingredient may be oxides and/or hydroxides such as MgO, $Mg(OH)_2$, ZnO, and the like.

The solid component may also comprise an organic salt source such as oxalate, lactate, malate, citrate, lactobionate compounds, and the like. The solid component may also comprise an acid source such as oxalic acid, lactic acid, malic acid, citric acid, lactobionic acid, and the like. The solid component may also comprise an organic compound such as an amino-acid, a polyol, a sugar, and the like.

The size of calcium phosphate particles was reported to significantly control the reactivity, thus possibly slowing the reaction and retarding the hardening or setting rate when too large. Granule size is related to the exposed surface area, and possibly influences the initial composition of the ingredients, the final dry product composition, and hence the mixing, mechanical and physical properties. Particle size, herein defined as an average particle size, may range from 0.2 microns to 100 microns, preferably is below 50 microns, and more preferentially varies from 0.1 to 20 microns.

Dry ingredients are combined together by physico-mechanical mixing techniques and instruments. This may be reached by a single mixing step, or by a series of mixing steps. The physico-mechanical mixing is not critical, may be operated with various techniques and instruments, but has to provide an intimate mixing of the dry ingredients. The mixing may be combined with a milling of solid minerals. Physico-mechanical mixing techniques include mortar, shaker mixing, ball planetary mixing, rolling mixing, vibratory mixing, and the like. A selection of the dry powder mixture may be operated following the dry mixing, for example by sieving into an appropriate ingredient size. Shaker (rotary) mixing and ball mixing was preferentially used in the present invention.

It is important that the dry ingredient mixing is achieved without chemically altering the ingredient reactivity, and without inducing unexpected reactions between the mixed ingredients. The intimate ingredient mixing regulates the further reactions between the different dry ingredients. Mixing must be performed until occurrence of a uniform dry mixture. To ensure anhydrous conditions, the mixing of dry ingredients may be operated under strict anhydrous conditions (gas, environment control), or in anhydrous non-aqueous liquids, for example solvents such as hexane or absolute alcohols, all traces of water being preliminarily eliminated from this liquid. Identically, the dry mixture is preferentially stored under strict anhydrous conditions so as to avoid any contamination or cross-reaction with water. Solid additives, being organic or inorganic, may be admixed with the dry ingredients at the dry mixing step. Incorporation of bioactive agents in the solid component may be performed during the dry mixing, or later, during a second mixing step.

Preparation of Self-Setting Hybrid Compositions/Bio-Materials

In the present invention, self-setting compositions are prepared by intimately mixing the liquid component and the powder component. Mixing may be performed manually by kneading, or physico-mechanically by using homogenizers, mixers or mills. There is no special preference for the mixing instruments, but the composition must be as uniform and homogeneous as possible. A specially designed instrument may be used as well as to mix and deliver the composition before use.

The liquid component is one selected among those previously described. One preferred basic liquid components comprise water, acid, chitosan and a first source of phosphate, glycerophosphate. Acid is generally selected among hydrochloric acid, glycerophosphoric acid, phosphoric acid, citric acid, acetic acid, lactic acid, and the like. The starting acidic aqueous medium is generally a 0.05 to 1N acid/water solution, and preferably a 0.05 to 0.5N solution. Chitosan is generally selected among partially N-deacetylated poly(glucosamine) having a deacetylation degree between 60 and 100%, preferably between 30 and 99% and more preferentially between 84 and 98%. It is present in the liquid component at a concentration ranging from 0.1% to 10% w/v, and more preferably between 0.1% and 2.0% w/v. The source of phosphate is generally an organic monophosphate dibasic salt, such as glycerol-2-phosphate and/or glycerol-3-phosphate sodium or magnesium salts, at a concentration between 0.1% and 20% w/v, and ideally between 1.0% and 10% w/v. The pH of the liquid component varies between 6.5 and 7.4, and preferably between 6.8 and 7.2. The viscosity of the liquid component is ranging between 5 mPa·s to 100,000 mPa·s, and preferably between 10 mPa·s and 1,000 mPa·s. As previously described, additional reagents may be an organic monosulfonate salt and/or a second hydrophilic polymer, and/or an organic molecules, and/or a bioactive agent. The liquid component is preferably stored at cool temperatures, ideally between 0 and 4° C.

The preferred calcium phosphates of the powder component comprise dry mixtures of apatitic calcium phosphate and/or tetracalcium phosphate, and/or tricalcium phosphate (alpha, beta, others), and/or dicalcium phosphate (hydrated or anhydrous) and/or monocalcium phosphate (hydrated or anhydrous). Apatites comprise sintered hydroxyapatite $Ca_{10}(PO_4)_6(OH)_{2-2x}O_x$ (SHA, Ca/P=1.67), precipitated hydroxyapatite $Ca_{10}(PO_4)_6(OH)_2$ (PHA, Ca/P=1.67), all calcium-deficient apatites such as the apatite of formula $Ca_9(HPO_4)(PO_4)_5OH$ (CDA, Ca/P=1.5), and the like or derivatives thereof. Calcium deficient apatites are apatitic calcium phosphates with Ca/P molar ratio in the range 1.66 to 1.5 or less. Compounds including interlayers of octacalcium phosphate are included.

In one embodiment, the solid component comprises a dry mixture of alpha-tricalcium phosphate and an apatitic calcium phosphate.

In another embodiment, the solid component comprises a dry mixture of alpha-tricalcium phosphate and an octacalcium phosphate.

Still in another embodiment, the solid component comprises alpha-tricalcium phosphate and an apatitic calcium phosphate and one of dicalcium phosphate and monocalcium phosphate.

In another embodiment, the solid component comprises a noncalcium phosphate salt.

In yet another embodiment, the solid component comprises a carbonated and/or a fluorinated and/or a strontium-containing and/or a magnesium-containing and/or a zinc-containing and/or a barium containing compound. This includes carbonate, fluoride or strontium, magnesium, zinc, barium salts with no calcium and phosphate as well as apatitic and nonapatitic calcium phosphates containing carbonate and/or fluoride and/or strontium and/or magnesium and/or zinc and/or barium.

The solid component also comprises an organic salt source such as oxalate, lactate, malate, citrate, gluconate compounds, and the like. The solid component also comprises an acid source such as oxalic acid, lactic acid, malic acid, citric acid, gluconic acid, and the like. The solid component also comprises an organic compound, being not an acid or a salt, such as an amino-acid, a polyol, a sugar, and the like.

In one embodiment, the solid component comprises a dry mixture of alpha-tricalcium phosphate and calcium deficient apatite. In another embodiment, the solid component comprises a dry mixture of alpha-tricalcium phosphate and calcium deficient apatite with at least one of an organic acid, an organic salt, an organic (nonacid, nonsalt) compound and a noncalcium phosphate salt.

The mineral ingredients of the solid component are dry-mixed as previously described so as to obtain a homogeneous dry mixture. This dry mixture can be performed in several distinct sequences. Preferentially, the dry minerals or ingredients were mixed-milled in a ball mill so as to obtain a mineral powder mixture homogeneous and of the adequate size. This mixing/milling may be performed in acetone or hexane solvent to avoid any moisture. An appropriate size of dry ingredient ranges between 1 and 250 μm, generally between 1 and 50 μm, and preferably between 1 and 20 μm.

The calcium to phosphate ratio of the solid component generally varies between 1.0 and 4.0, and typically between 1.0 and 2.0, and preferably between 1.2 and 1.8.

The mixing of liquid (L) and solid (S) components is performed at a liquid/solid weight ratio between 0.05 and 1.50 (mL/g), and preferably between 0.2 and 1.0 (mL/g).

The liquid component is endothermally sensitive, but the resulting paste is self-setting with time, thus self-hardening at 37° C. and 100% humidity into a solid bio-materials that looks like a ceramic or cement-like materials. The cement-like materials have higher compression strengths: after two days ageing in a water solution, the wet ultimate compression strength reaches typically 5-10 MPa and up. Resulting mineral composition includes apatite. The material is resorbable in situ over a period of 18 months.

Bioactive Ingredients

Any bioactive ingredients may be incorporated and released from self-setting compositions and bio-materials. The incorporation can be assessed out via the liquid or solid component. Bioactive agents include drugs, therapeutic agents, osteogenic agents and anti-resorptive agents. Bioactive agents of interest are typically osteoinductive agents selected from a group comprising growth factors, hormones, individual osteoinductive proteins and mixtures of osteoinductive proteins, bone derived materials including demineralized bone matrix (DBM) or powder (DBP), growth factors selected from a group comprising IGF, EGF, a-FGF, b-FGF, PDGF-A, PDGF-B and/or TGF-beta, bone morphogenic proteins (BMP), sialoproteins, osteonectin, osteopontin, osteocalcin, calcitonin, or a mixture thereof. Other agents include antibiotic, antiviral, antitumor, and/or immuno-supressive agent.

Mode of Administration—Application

The administration of the composition to hard-tissue defects, cavities, or any anatomical structures is performed percutaneously by injection through a cannula, trocar or needle of a gauge ranging from 7 to 27, preferably from 14 to 22, and more ideally from 16 to 22, and with the use of syringe or a pressure injecting device, or by the use of endoscopic technique and instrument or during the course of an open surgical operation.

The compositions may be useful for medical and dental indications, in human or veterinarian procedures. They may be used in one of the following procedures:

a) to favor and promote regeneration and/or repair of bone lost due to disorders, diseases or deficiencies; to replace bone that is surgically removed or lost during a trauma;

b) to reconstruct, (re)shape and/or replace partly or totally hard-tissues;

c) to favor the repair of fractured bones; to fix bone fragments;

d) to ensure retention and strength in situ of other orthopaedic devices (pin, prosthesis, fixation);

e) to protect or cap the dental pulp;

f) to fill permanently or temporarily enamel and dentin;

g) to fill root canals;

h) to implant or replant a teeth; and i) to act a luring cement in dentistry and orthopaedic surgery.

More generally, the compositions may be useful for all repair, regeneration, filling, replacement procedures associated to hard-tissues as well as for delivering drugs or bioactive agents to hard-tissues.

The composition can be injected to the filling and repair of internal bone cavity, of local treatment of osteoporotic bones, and other demineralized bones and demineralization disorders; of bone defects or cavities, for example in the case of periodontal defects with bone loss, augmentation of the alveolar ridge or surgically-performed hard-tissue defects following resection of diseased hard-tissue parts; of bone fractures for repairing fractures, fixing bone fragments, delivering agents that accelerate the sequence of fracture healing.

Self-setting mineral-polymer compositions are to be used in orthopaedic, cranio-maxillofacial or dental surgery.

The present invention will be more readily understood by referring to the following examples, which are given to illustrate the invention rather than to limit its scope.

EXAMPLE I

Preparation of Liquid Phases

The liquid phase of bone composition is an endothermally self-forming aqueous solution made of one hydrophilic biopolymer and at least one water-soluble phosphate source.

A representative liquid phase is a chitosan/glycero-phosphate [chitosan-GP] aqueous solution. An acidic chitosan aqueous solution (2.0% w/v) was made with a chitosan previously deacetylated at 83-97%, filtered and dialyzed, and was prepared from a 0.097M (0.10M) HCl solution. A chitosan/glycerophosphate aqueous solution was prepared from the 2.0% (w/v) chitosan in HCl aqueous solution and a 8.4% (w/v) disodium glycerophosphate in distilled water solution. Final concentrations (w/v) in the self-gelling chitosan/glycerophosphate systems was approximately 1.6-2.0% (chitosan) and 6.75-8.2% (glycerol-phosphate).

Glycerophosphate salts act herein as buffering/thermo-gelling agents for the chitosan solution. Other buffering/thermogelling phosphate sources may be used, typically organic monobasic phosphate salts, such as glucose-phosphate or fructose-phosphate salts. Other buffering agents may be also associated with glycerophosphate salts so as to enhance the buffering/thermogelling action such as amino acids or organic sulfonate salts. Table 1 summarizes the potent composition of liquid phases.

TABLE 1

Buffering/thermogelling agents for liquid phases having 1.0-2.0% by weight of chitosan

| Buffering/Thermogelling agents | Example contents (% w/v) | Remarks |
|---|---|---|
| Glycero-phosphate salts | 4-10 | |
| Glucose-phosphate salts | 6-12 | |
| Fructose-phosphate salts | 1-6 | |
| Histidine | 2-10 | Histidine and glucosamine used as co- |
| Glucosamine | 2-10 | buffering agent with glycero-phosphate. |
| BIS-TRIS | 1-8 | Used alone or mixed with glycero-phosphate. |
| MES (sulfonate) salt | 1-4 | Used alone or mixed with glycero-phosphate. |
| HEPES (sulfonate) salt | 1-4 | Used alone or mixed with glycero-phosphate. |
| TES (sulfonate) salt | 1-4 | Used alone or mixed with glycero-phosphate. |

Histidine was typically admixed with GP in the chitosan solution (Ex: 1.5% w/v chitosan, 4.0% w/v GP+4.0% w/v histidine). BIS-TRIS may be used alone as a buffering/thermogelling agent (Ex: 1.5% w/v chitosan+2.0% w/v BIS-TRIS). HEPES, TES or MES sulfonate agent may be used alone as a buffering/thermogelling agent (Ex: 1.5% w/v chitosan+2.0% w/v HEPES, TES or MES).

a) Addition of a Second Water-Soluble Polymer in the Liquid Phase

A second water-soluble polymer may be dissolved in the chitosan-GP aqueous solution. Table 2 gives the composition of liquid phase consisting in chitosan-GP plus a water-soluble polymer. Glycerophosphate may be added prior to the dissolution of the second polymer, or after the dissolution of the second polymer.

Thermosensitive polymers such as the methyl cellulose, hydroxypropyl methyl cellulose or Pluronic® were found to be the more sensitive to the concentration in glycerophosphate salts. Those salts were found to affect the gelling or precipitating temperature of the polymer, thus leading to a precipitation of the chitosan/GP/polymer(2) system.

TABLE 2

Liquid phase compositions having an admixed second water-soluble polymer

| Polymer (2) | Polymer content (w/v) | Chitosan content (w/v) | GP content (w/v) | Remarks |
|---|---|---|---|---|
| Hydroxyethyl Cellulose | 1.0% | 2.0% | 8.0% | Form gels. |
| Hydroxypropyl Methyl Cellulose | 0.55% | 1.0% | 4.5% | Form gels. |
| Polyethylene glycol | 1.0% | 2.0% | 8.0% | Form gels. |
| Methyl Cellulose | 1.0-2.0% | 1.0-2.0% | 4.0-6.0% | Form gels. Precipitation may occur with higher GP contents. |
| Pluronic ® | 1.0% | 2.0% | 2.0% | Form gels. Precipitation may occur with higher GP contents. |
| Collagen (type I) | 1.0% | 1.0% | 8.0% | Form gels. |

All presented concentrations (%, mol/l . . . ) are final.

All polymers (2) were dissolved in a prepared chitosan-GP solution, except for collagen, and more generally polyamines, that are dissolved in combination with the chitosan.

b) Addition of Water-Soluble Ingredients of Interest

Some organic molecules that are soluble or miscible with water may be added to the chitosan-based liquid phase to give modified or improved physico-chemical characteristics, mechanical or handling performances, or biological properties. This includes polyols, sugars, amino-acids, polysaccharides, and other biochemicals.

Polyols & Sugars

Of particular interest may be the polyols such as polyols having diol hydrocarbon moieties, which may be useful for the processing, or the performances of the liquid phase. Among those polyols, glycerol, mannitol, sorbitol and ethylene glycol compounds such as the triethylene glycol, tetraethylene glycol (Table 3) were found to be good representative examples, being attractive and bringing modifications or improvements to the liquid phase or resulting thermo-formed gel. Sugars such as fructose, glucose, etc may be used similarly.

TABLE 3

Liquid phase compositions having added water-soluble non-polymeric ingredient (Polyols)

| Polymer (2) | Ingredient content (w/v) | Chitosan content (w/v) | GP content (w/v) | Remarks |
|---|---|---|---|---|
| Glycerol | 0.1-1.0 | 2.0% | 8.0% | Form gels. Changed rheological parameters of gels. Stabilize chitosan sol viscosity. |
| Sorbitol (Mannitol) | 0.1-1.0 | 1.0% | 4.0% | Form gels. Changed rheological parameters of nonsterile gels. Stabilize chitosan sol viscosity. |
| Ethylene glycol | 0.1-1.0 | 2.0% | 8.0% | Form gels. Changed rheological parameters of nonsterile gels. Stabilize chitosan sol viscosity. |
| Tri-(Tetra-)ethylene glycol | 0.1-1.0 | 2.0% | 8.0% | Form gels. Changed rheological parameters of gels. Stabilize chitosan sol viscosity. |

All presented concentrations (%, mol/l . . . ) are final.

Polysaccharides (GAGS)

Other water-soluble (bio)chemical ingredients may be of interest to be added to the chitosan-GP liquid phase. However, such ingredients must not disturb the chitosan-GP composition (ingredient) and its thermogelling property.

Glycoaminoglycans may be added to the chitosan-GP solution to a certain extent. It must be taken care of not inducing precipitation of chitosan. Heparin (see Table 4) was used as the GAGs to be added. Chitosan solutions were 4.0% w/v chitosan (deacetylation 95%) in 0.19M HCl. GP solutions were 54.6% w/v in water. Heparin in water solutions was at 1 mg/mL (A), 0.1 mg/mL (B), 10 µg/mL (C) and 1 µg/mL (D).

TABLE 4

Liquid phase compositions having added water-soluble non-polymeric ingredient (Heparin)

| # | Composition | pH | Remarks |
|---|---|---|---|
| 1. | 500 μL chitosan + 150 μL GP 250 μL water + 100 μL Heparin (B) | 7.04 | Gels. |
| 2. | 500 μL chitosan + 250 μL water 150 μL GP + 100 μL Heparin (C) | 7.01 | Gels. |
| 3. | 500 μL chitosan + 250 μL water 150 μL GP + 100 μL Heparin (B) | 6.87 | Gels. |
| 4. | 500 μL chitosan + 250 μL water 150 μL GP + 100 μL Heparin (A) | 6.97 | Reduced precipitation. Gels. | c) Addition of a Second Water-Soluble Phosphate Source to the Liquid Phase

An acidic chitosan aqueous solution (2.0-4.0 w/v) was made with a chitosan deacetylated at 83-85%, filtered and dialyzed, and was prepared from a 0.1M HCl solution (see Table 5).

TABLE 5

Composition of liquid phases supplemented with a second source of water-soluble phosphate

| Composition | pH | Chitosan:GP (% w/v) | [Phosphate] mol/l | Gelling time (initial) | Precipitation |
|---|---|---|---|---|---|
| 10 ml chitosan-GP | 7.0 | 2.0:8.2 | 0 | 30 minutes | No |
| 8 ml chitosan-GP + 2 ml phosphate (1) | 6.9 | 1.6:6.6 | 0.0014 | 30 minutes | No |
| 7 ml chitosan-GP + 3 ml phosphate (1) | 6.9 | 1.4:5.7 | 0.0021 | 30 minutes | No |
| 5 ml chitosan-GP + 5 ml phosphate (1) | 6.9 | 1.0:4.1 | 0.0035 | 30 minutes | No |
| 8 ml chitosan-GP + 2 ml phosphate (2) 1:1 | 6.9 | 1.6:6.6 | 0.04 | Slow gelation | No |
| 7 ml chitosan-GP + 3 ml phosphate (2) 1:1 | 6.9 | 1.4:5.7 | 0.06 | Slow gelation | No |
| 5 ml chitosan-GP + 5 ml phosphate (2) 1:100 | 6.95 | 1.0:4.1 | 0.001 | 30-40 minutes | No precipitation |

All presented concentrations (%, mol/l . . . ) are final.

A chitosan-GP aqueous solution was prepared from a pre-cooled (4° C.) chitosan in HCl solution and a 54-55% (w/v) disodium glycerophosphate (GP) in distilled water solution. The pH of the resulting liquid chitosan-GP solution was measured at 21° C.

A phosphate solution (1) was prepared with 0.144 g/l $KH_2PO_4.7H_2O$ potassium dihydrogen phosphate hydrated) and 0.795 g/l $Na_2HPO_4$ disodium hydrogen phosphate) and had a pH of 7.4 at 20° C. Amounts of the chitosan-GP solution and phosphate solution (1) were admixed homogeneously, then the pH of the resulting solutions was measured (Table 6). The solutions were finally disposed at 37° C. for gelation, all signs of precipitation being noted. All chitosan-GP+phosphate solution (1) (80:20 to 50:50, vol) showed no signs of precipitation, and gelled within 30 minutes at 37° C.

TABLE 6

Composition of liquid phases supplemented with a second source of water-soluble phosphate

| Composition | pH | Chitosan:GP (% w/v) | [Phosphate] mol/l | Gelling time (initial) | Precipitation |
|---|---|---|---|---|---|
| 10 ml chitosan-GP | 7.0 | 4.0:8.2 | 0 | 30 minutes | No |
| 9 ml chitosan-GP + 1 ml phosphate (3) | 6.7 | 3.6:7.4 | 0.05 | | More turbid |
| 8 ml chitosan-GP + 2 ml phosphate (3) | 6.7 | 3.2:6.6 | 0.1 | | Highly turbid; Gels heterogeneously |

A concentrated phosphate solution (2) was prepared from 283.92 g/l of $Na_2HPO_4$ (0.2 mol/l disodium hydrogen phosphate) and 239.96 g/l of $NaH_2PO_4$ (0.2 mol/l sodium dihydrogen phosphate) and had a pH of 7.4 at 37° C. This phosphate solution was used with dilutions at 1:1, 1:10, 1:100 and 1:1000. Equal volumes (50:50) of the diluted to concentrated phosphate solution (2) and chitosan-GP solution were mixed homogeneously. The pH of the resulting solutions was measured, and the solutions disposed at 37° C. for gelation, all signs of precipitation being noted. All chitosan-GP/phosphate (2) gelled with various rates at 37° C.

A more concentrated phosphate solution (3) was prepared: 0.5 mol/l $NaH_2PO_4$ (600 g/l) and 0.5 mol/l $Na_2HPO_4$ (709.8 g/l). Volumes of the concentrated phosphate solution (3) was added to chitosan-GP solutions, and mixed homogeneously. The pH of the resulting solutions was measured, and the solutions disposed at 37° C. for gelation, all signs of precipitation being noted. Chitosan-GP is fully compatible with 5 mM PBS solution at pH 7.2-7.4. Compatibility depends upon the phosphate content (Tables 2-4): the addition of highly concentrated phosphate solutions (especially dibasic phosphates) renders the chitosan-GP system more turbid and prone to precipitation or heterogeneous gelation.

d) Addition of a Water-Soluble Carbonate Source to the Liquid Phase

The chitosan-GP solutions were prepared as in Example 1c). A carbonate solution was prepared from a 0.2 mol/l solution of monosodium carbonate, having a pH of 8.16 at 21° C. Equal volumes (50:50) of the diluted (1/10) to concentrated carbonate solution and chitosan-GP solution were mixed homogeneously. A carbonate (0.1 mol/l)+phosphate (0.1 mol/l) solution was also used. The pH was measured, and the solutions were disposed at 37° C. for gelation, all signs of precipitation being noted. Chitosan-GP systems are fully compatible with carbonate buffer such as a 5 mM phosphate/carbonate buffer at a pH of 8.8. But, this compatibility will decline for too high carbonate contents.

In Examples 1e) and 1f) below, liquid chitosan-GP formulations supplemented with water-soluble phosphates and/or carbonates (Table 7) present a reduced shell-life and stability, even at low temperatures (4° C.). This is dose-dependent, the more concentrated is the content of water-soluble phosphate and/or carbonate in the chitosan-GP formulation, the less stable is the resulting solution.

TABLE 7

Composition of liquid phases supplemented with a source of water-soluble carbonate

| Composition | pH | [Carbonate] mol/l | Gelling time (initial) | Precipitation/ Remarks |
|---|---|---|---|---|
| 10 ml chitosan-GP | 7.0 | 0 | 30 minutes | No |
| 8 ml chitosan-GP + 2 ml carbonate | 7.0 | 0.04 | 30 minutes | No |
| 6 ml chitosan-GP + 4 ml carbonate | 7.1 | 0.08 | 30 minutes | No. Some sparse complexes may occur by the surface. |
| 5 ml chitosan-GP + 5 ml carbonate | 7.1 | 0.10 | 30 minutes | No. Fibrous complexes occur sparsely at the upper level. |
| 5 ml chitosan-GP + 5 ml carbonate 1:10 | 6.95 | 0.01 | 30 minutes | No |

All presented concentrations (%, mol/l . . . ) are final.

e) Typical Preparation of Sterile Liquid Phase

Sterile Liquid Phases

Sterilization of liquid phase can be performed during the preparation and processing of the chitosan-GP solutions. The chitosan-GP systems can not be sterilized by energizing methods, due to unexpected and undesirable thermal gelling. Chitosan solutions (no GP) and GP solutions (no chitosan) are to be sterilized separately. GP aqueous solutions have no viscosity and are sterilized by filtration in all cases, without any noticeable adverse effects. Chitosan materials (solid) or chitosan solutions (acidic aqueous medium) must be sterilized while avoiding the occurrence of degradative effects on both chitosan polymer and chitosan-GP systems. Table 8 illustrates the effects of sterilizing on Chitosan-GP systems (no additive).

TABLE 8

Effects Of Sterilizing On Chitosan-Gp Systems (No Additive)

| Chitosan sterilization | Effects on chitosan biopolymer | Effect of thermogelling Chitosan-GP systems. |
|---|---|---|
| Autoclaving of chitosan solutions in acidic media. | Controlled modification; | Gels (slightly decreased gelling rate). |
| Autoclaving of chitosan suspension in water. | Controlled modification; | Modify gel properties. |
| Irradiation of chitosan materials (4° C.). | Controlled modification; | Gels (slightly decreased gelling rate). |
| Irradiation of chitosan materials (20° C.). | Stronger modification; | Gels (affect the gelling rate). |

EXAMPLE II

Cement-Like Compositions and Bio-Materials

Compositions for cement-like bio-materials were prepared from liquid and solid (mineral) phases, liquid phases being prepared typically as described in Examples 1 and being thermally sensitive. The solid phase is a powder phase, generally containing minerals such as calcium phosphates or carbonates, and optionally solid organics. Liquid and solid phases are intimately mixed together before reaching a cement-like self-setting composition that has a hardening characteristic.

Tetracalcium phosphate (TTCP) was from Clarkson Chromatography Products Corp. (NY, USA). Dicalcium phosphate and Tricalcium phosphate (alpha or beta) were from Fluka Chemical Company (Germany) and Clarkson Chromatography Products Corp. (NY, USA). Monocalcium phosphates were from American & Chemical (USA) and Aldrich Chemical Company.

a) TCP Cement-Like Compositions and Resulting Bio-Materials

TCP/MCP Calcium Phosphate Content

Liquid phases were composed of pure water or phosphate aqueous buffer (used as control for normal cement-like materials), pure chitosan-GP aqueous systems (see Example 1) or chitosan-GP/phosphates, chitosan-GP/carbonates or chitosan-GP/phosphates-carbonates aqueous systems (see Examples 1a-1d).

Solid TCP/MCP phases were prepared from tri-calcium phosphates (α- or β-TCP) and mono-calcium phosphates (anhydrous or hydrated), but optionally also contained other mineral ingredients (carbonated, fluorinated) (see Table 9).

TABLE 9

Composition of liquid and solid phases for TCP/MCP/CC based cement-like bio-materials

| Mineral Phase | Ca/P | Liquid Phase | L/S ml/g | Observations |
|---|---|---|---|---|
| βTCP/MCPM | 1.45 | Water | 0.6 | Set.: 3 h; hard.: 4 (24 h) |
| | | Gelling CGP (1% C) | 0.6 | Set.: 3 h; hard.: 4 (24 h) |
| βTCP/MCPM | 1.45 | NaPO4 0.01M | 0.45 | Set.: 1 h; hard.: 5 (20 h) |
| | | Gelling CGP (1% C), NaP 0.01M | 0.45 | Set.: 1 h; hard.: 4 (20 h) |
| βTCP/MCPM/ HAP | 1.59 | Gelling CGP (1% C) | 1 | Set.: 4 h; hard.: 2 (24 h) |
| | | Gelling CGP (1% C), NaP 0.01M | 1 | Set.: 2 h; hard.: 3 (24 h) |
| βTCP/MCPM/ CaCO$_3$ | 1.59 | Gelling CGP (1% C) | 0.40 | Set.: 1 h; hard.: 5 (24 h) |
| | | Gelling CGP (1% C), NaP 0.01M | 0.40 | Set.: 1 h; hard.: 5 (24 h) |
| βTCP/MCPM | 1.33 | Water | 0.3 | Set.: 30 s; hard.: 5 (2 min) |
| | | Gelling CGP (1% C) | 0.3 | Set.: 30 s; hard.: 5 (2 min) |
| βTCP/MCPM/ HAP | 1.45 | Water | 1.4 | Set.: 1 h; hard.: 2 (24 h) |
| | | Gelling CGP (1% C), | 1 | Set.: 1 h; hard.: 2 (24 h) |
| βTCP/MCPM/ CaCO$_3$ | 1.41 | Water | 0.4 | Set.: 1 h; hard.: 5 (4 h) |
| | | Gelling CGP (1% C) | 0.4 | Set.: 1 h; hard.: 3 (2 h) |
| βTCP/MCPM/ DCPA | 1.00 | Gelling CGP (1% C) | 0.40 | Set.: 1 h; hard.: 5 (1 h) |
| βTCP/Citric ac. | 1.50 | Gelling CGP (1% C) | 0.40 | Set.: 20 h; hard.: 5 (24 h) |
| βTCP/MCPM/ Citric ac. | 1.45 | Gelling CGP (1% C) | 0.40 | Set.: 3 h; hard.: 5 (24 h) |
| βTCP/MCPM/ NaH$_2$PO$_4$ | 1.45 | Gelling CGP (1% C) | 0.30 | Set.: 1 h; hard.: 3 (24 h) |

S/L ratio: is given in ml of liquid phase per gram of solid phase.
Ca/P*: Total Ca/P ratio for solid phase.
Hardness: from 0 (liquid) to 5 (very hard).

In given examples (see Table 9), a composition was consisting in TCP, MCP and calcium carbonate (CC), thus giving at the end a carbonated apatite material that can be represented by $Ca_{9-x}(HPO_4)_{1-1.5x}(PO_4)_{5-2.5x}(CO_3)_{3.5x}(OH)_{1+1.5}x$. Typical solid TCP powder phase compositions were made of 100% TCP, and 80-90% wt. TCP (Ex: 7.77 g), 5-10% wt. MCP (Ex: 0.86 g) and 5-10% wt. CC (Ex: 0.86 g). Another typical example consisted in 4.2 g TCP, 1.3 g MCP and 1.2 g Calcium Sulfate dihydrate (CS). Ca/P ratio varied from 1.54 to 2.64. TCP was α or β (here for example, β-TCP was selected), α-TCP being potentially more reactive.

Solid TCP based phases were obtained by dry-mixing of mineral powders, either by manual mixing or rotative mixing. Manual mixing was done by using a mortar and pestle. Rotative mixing was performed at low speeds in closed 50 cc chambers that contained 10 cc to 30 cc of mineral materials (~50% free volume). Powder mixture was stored under strict anhydrous conditions (<10% HR). The liquid phase was added to the solid powder phase in a glass or agate recipient. Typically, 1 gram of solid minerals was admixed with the required amount of liquid phase (see Table 10). Intimate mixing was reached manually by kneading, or mechanically (shear mixing, ball mill mixing). Once being well-homogeneized, the resulting paste or suspension was shaped in a mold, with a size: approximately mm long×mm width×mm deep, and disposed in a closed humid chamber (~100% humidity) at 37° C.

TABLE 10

Composition of liquid and solid phases for TCP/MCP based cement-like bio-materials

| Mineral Phase | Ca/P | Liquid Phase | L/S ml/g | Observations |
|---|---|---|---|---|
| βTCP/ DCPA | 1.45 | Water | 0.45 | Set.: 5 h; hard.: 3 (24 h) |
| | | Gelling CGP (C 1%) | 0.45 | Set.: 2 h; hard.: 2 (24 h) |

TABLE 10-continued

Composition of liquid and solid phases for TCP/MCP based cement-like bio-materials

| Mineral Phase | Ca/P | Liquid Phase | L/S ml/g | Observations |
|---|---|---|---|---|
| βTCP/ DCPA | 1.45 | NaPO4 0.01M | 0.40 | Set.: 19 h; hard.: 1 (24 h) |
| | | Gelling CGP (C 1%), NaP 0.01M | 0.40 | Set.: 2 h; hard.: 2 (24 h) |
| βTCP/ DCPA/ HAP | 1.59 | Gelling CGP (C 1%) | 1.0 | Set.: 2 h; hard.: 2 (24 h) |
| | | Gelling CGP (C 1%), NaP 0.01M | 1.0 | Set.: 2 h; hard.: 2 (24 h) |
| βTCP/ DCPA/ CaCO$_3$ | 1.59 | Gelling CGP (C 1%) | 0.40 | Set.: 1 h; hard.: 4 (24 h) |
| | | Gelling CGP (C 1%), NaP 0.01M | 0.40 | Set.: 1 h; hard.: 4 (24 h) |

S/L ratio: is given in ml of liquid phase per gram of solid phase.
Ca/P*: Total Ca/P ratio for solid phase.
Hardness: from 0 (liquid) to 5 (very hard).

TCP/DCP Calcium Phosphate Content

The composition and preparation were identical to those described previously in Example 2a, except that monocalcium phosphate (MCP anhydrous or hydrated) was replaced by di-calcium phosphate (DCP anhydrous or hydrated). One typical example comprises 3.10 g TCP and 0.30 g DCP. Other mineral ingredients may be incorporated in the solid phase: in the Examples (see Table 11), calcium carbonate minerals were added, thus giving carbonated apatites. The Ca/P ratio of compositions was between 1.40 and 1.60.

b) TTCP Cement-Like Compositions and Bio-Materials
TTCP/MCP Calcium Phosphate Contents Liquid phases were composed of pure phosphate aqueous buffer (control), chitosan-GP aqueous systems (see Examples 1), chitosan-GP/phosphates, chitosan-GP/carbonates or chitosan-GP/phosphates-carbonates aqueous systems (see Examples 1a-1d).

Phosphate buffer was 0.2 mol/l sodium or potassium hydrogen phosphates (Ex: $NaH_2PO_4+K_2HPO_4$). Phosphate addition to chitosan-GP systems was done with sodium or potassium hydrogen phosphates (Ex: NaH$_2$PO$_4$+K$_2$HPO$_4$) (see Examples 1). Carbonate addition to chitosan-GP systems was done with sodium bicarbonate (NaHCO$_3$) (see Examples 1).

based phases were prepared from tetra-calcium phosphates (TTCP) and di-calcium phosphates (DCP Anhydrous or Di-hydrated), but optionally also contained other mineral ingredients (carbonated, fluorinated). Powder mixture of TTCP and DCP was equimolar (see Table 12).

TABLE 12

Composition of liquid and solid phases for TTCP/DCP based cement-like bio-materials

| Mineral Phase | Ca/P | Liquid Phase | L/S ml/g | Observations |
|---|---|---|---|---|
| TTCP/DCPA | 1.66 | Water | 0.60 | Set.: 24 h; hard.: 1 (24 h) |
|  |  | Gelling CGP (C 1%) | 0.50 | Set.: 3 h; hard.: 3 (24 h) |
| TTCP/DCPA | 1.66 | NaP 0.01M | 0.40 | Set.: 3 h; hard.: 2 (20 h) |
|  |  | Gelling CGP (C 1%), NaP 0.01M | 0.40 | Set.: 3 h; hard.: 2 (20 h) |
| TTCP/DCPA/HAP | 1.66 | Gelling CGP (C 1%) | 0.75 | Set.: 2 h; hard.: 5 (5 h) |
|  |  | Gelling CGP (C 1%), NaP 0.01M | 1.00 | Set.: 2 h; hard.: 3 (24 h) |
| TTCP/DCPA/CaCO$_3$ | 1.75 | Gelling CGP (C 1%) | 0.50 | Set.: 19 h; hard.: 2 (24 h) |
|  |  | Gelling CGP (C 1%), NaP 0.01M | 0.50 | Set.: 19 h; hard.: 2 (24 h) |
| TTCP/DCPA/Citric ac. | 1.66 | Gelling CGP (C 1%) | 0.30 | Set.: 1 h; hard.: 6 (1 h) |
| TTCP/DCPA/NaH$_2$PO$_4$ | 1.66 | Gelling CGP (C 1%) | 0.80 | Set.: 1 h; hard.: 5 (1 h) |

S/L ratio: is given in ml of liquid phase per gram of solid phase.
Ca/P*: Total Ca/P ratio for solid phase.
Hardness: from 0 (liquid) to 5 (very hard).

TABLE 11

Composition of liquid and solid phases for TTCP/DCP based cement-like bio-materials

| Mineral Phase | Ca/P | Liquid Phase | L/S ml/g | Observations |
|---|---|---|---|---|
| TTCP/MCPM | 1.66 | Water | 0.70 | Set.: 1 h; hard.: 5 (5 h) |
|  |  | Gelling CGP (C 1%) | 0.70 | Set.: 1 h; hard.: 5 (5 h) |
| TTCP/MCPM | 1.66 | NaP 0.01M | 0.60 | Set.: 1 h; hard.: 5 (4 h) |
|  |  | Gelling CGP (C 1%), NaP 0.01M | 0.60 | Set.: <1 h; hard.: 5 (4 h) |
| TTCP/MCPM/HAP | 1.66 | Gelling CGP (C 1%) | 1.00 | Set.: <1 h; hard.: 4 (24 h) |
|  | 1.66 | Gelling CGP (C 1%), NaP 0.01M | 1.00 | Set.: <1 h; hard.: 5 (5 h) |
| TTCP/MCPM/CaCO$_3$ | 1.75 | Gelling CGP (C 1%) | 0.6 | Set.: 1 h; hard.: 5 (4 h) |
|  | 1.75 | Gelling CGP (C 1%), NaP 0.01M | 0.6 | Set.: 1 h; hard.: 5 (4 h) |

S/L ratio: is given in ml of liquid phase per gram of solid phase.
Ca/P*: Total Ca/P ratio for solid phase.
Hardness: from 0 (liquid) to 5 (very hard).

Solid TTCP/MCP phases were prepared from tetra-calcium phosphates (TTCP) and monocalcium phosphates (MCP Anhydrous or Dihydrated), but optionally also contained other mineral ingredients (calcium, carbonated, fluorinated). Seeding of hydroxyapatite (HA) was also used (Ex: 40% wt.). In typical Examples, solid phases included 3.26 g TTCP and 0.71 g MCPM, or 3.26 g TTCP and 2.04 g MCPM. Ca/P ratio was ranging from 1.33 to 1.80. Solid TTCP/MCP phases were obtained by dry-mixing, either manual mixing or rotative mixing, of mineral powders. Manual mixing was done with a mortar and pestle. Rotative mixing was performed at low speeds in closed 50 cc chambers that contained 10-30 cc of mineral materials (~50% free volume).

TTCP/DCP Calcium Phosphate Contents

Figure 2:
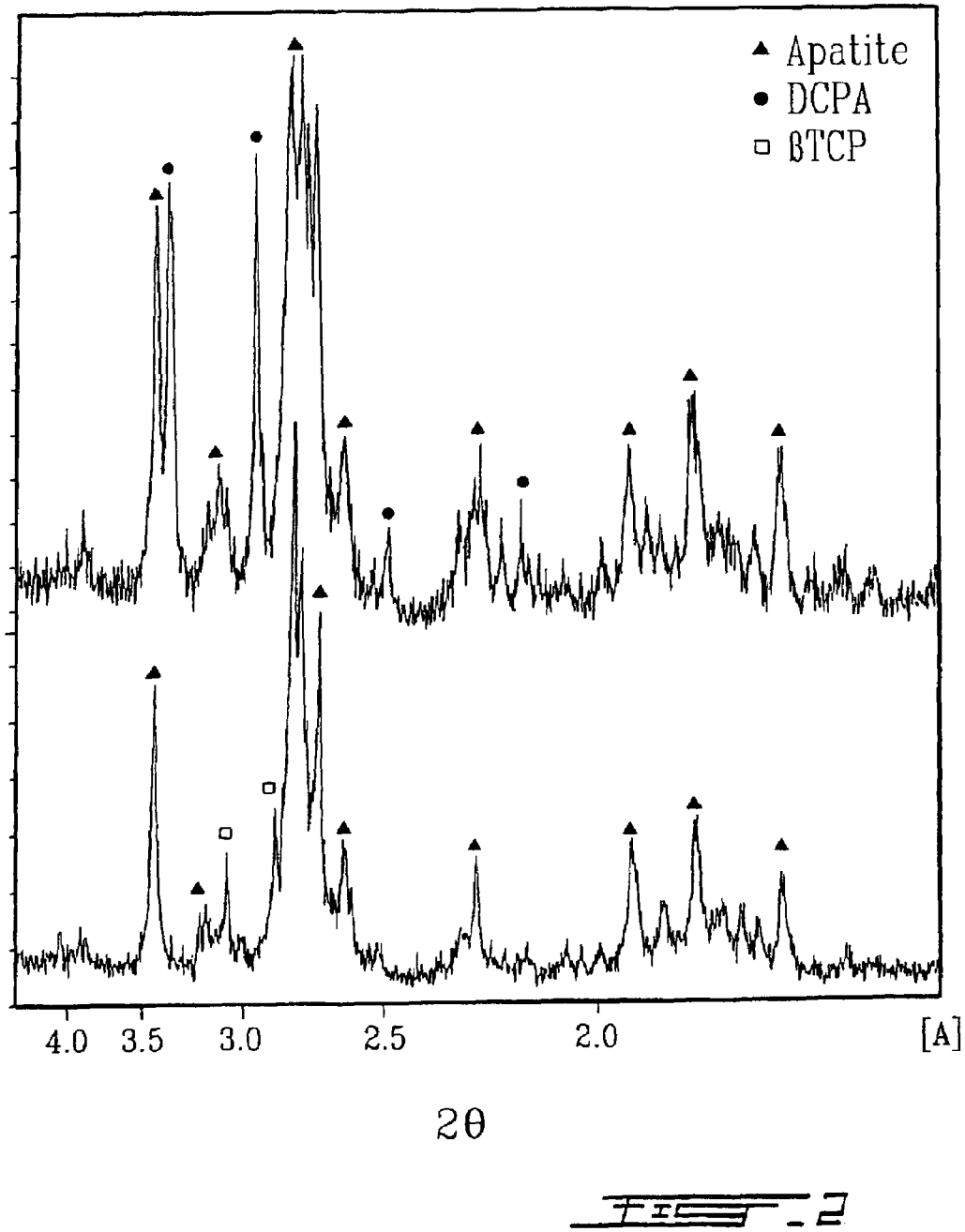
FIG. 2 illustrates X-ray diffraction graphs of self-setting mineral-polymer hybrid compositions (mineral), wherein signs ▲, ●, and □ correspond to bands for apatite, dicalcium phosphate (anhydrous) or tricalcium phosphate (beta)

TTCP/DCP mineral phases were also used to prepare cement-like compositions and bio-materials. TTCP/DCP Example solid phases contained 3.26 g TTCP and 1.36 g DCPA. A 40% (wt.) seeding of hydroxyapatite (HA) was also used with 1.63 g TTCP and 0.68 g DCPD. Ca/P ratio was about 1.67. Solid TTCP/DCP phases were obtained by dry-mixing, either manual mixing or rotative mixing, of mineral powders. Manual mixing was done with a mortar and pestle. Rotative mixing was performed at low speeds in closed 50 cc chambers that contained 10-30 cc of mineral materials (~50% free volume) (see FIG. 2).

c) TTCP/TCP Cement-Like Compositions and Bio-Materials

A solid mineral phase was prepared on the basis of a dry-mixture of TTCP and TCP minerals, by incorporating mono-calcium phosphate (MCP anhydrous or hydrated) or di-calcium phosphate (DCP anhydrous or hydrated). In Examples, 1.55 g TTCP and 3.1 g TCP were admixed for one composition (Ca/P ratio: 1.67) (see Table 13).

TABLE 13

Composition of liquid and solid phases for TTCP/TCP based cement-like bio-materials

| Mineral Phase | Ca/P | Liquid Phase | L/S ml/g | Observations |
|---|---|---|---|---|
| TTCP/βTCP | 1.66 | Water | 0.45 | Set.: 3 h; hard.: 3 (24 h) |
|  |  | Gelling CGP (C 1%) | 0.45 | Set.: 3 h; hard.: 3 (24 h) |
| TTCP/βTCP | 1.66 | NaP 0.01M | 0.40 | Set.: 19 h; hard.: 2 (24 h) |
|  |  | Gelling CGP (C 1%), NaP 0.01M | 0.40 | Set.: 19 h; hard.: 1 (24 h) |
| TTCP/βTCP/HAP | 1.66 | Gelling CGP (C 1%) | 1.0 | Set.: 4 h; hard.: 1 (24 h) |
|  |  | Gelling CGP (C 1%), NaP 0.01M | 1.0 | Set.: 2 h; hard.: 2 (24 h) |
| TTCP/βTCP/CaCO$_3$ | 1.75 | Gelling CGP (C 1%) | 0.40 | Set.: 19 h; hard.: 2 (24 h) |
|  |  | Gelling CGP (C 1%), NaP 0.01M | 0.40 | Set.: 19 h; hard.: 2 (24 h) |

S/L ratio: is given in ml of liquid phase per gram of solid phase.
Ca/P*: Total Ca/P ratio for solid phase.
Hardness: from 0 (liquid) to 5 (very hard).

TCP was either α- or β-tricalcium phosphate. Dry mixing was achieved as previously described in Example 2a-2b. Liquid phases were pure water or chitosan-GP aqueous systems. Admixing and homogenization of liquid and solid phases was done as previously reported in Examples 2a-2b.

d) Other Cement-Like Compositions and Bio-Materials

Other combinations of calcium phosphate minerals were performed to prepare the solid phase. Some given examples report the use of hydroxyapatite (HAP) crystal or other seeding (see Table 14).

Most compositions contains MCP, OCP calcium phosphates and/or calcium/zinc sources (oxides). Octa-calcium phosphate may be used, combined with calcium phosphates or calcium sources, in the solid mineral phase. OCP (4.91 g) was admixed with $Ca(OH)_2$ (0.37 g) and a 40% wt. HAP seeding, or with 3.26 g TTCP and a 40% wt. HAP seeding. Mixing of mineral powders and homogenization of liquid and solid phases were performed as previously described. Monocalcium phosphate may be incorporated as a major calcium phosphate source. In typical Examples, 2.52 g MCPM was admixed with 1.31 g CaO (40% wt. HAP seeding), or with 3.10 g TCP (10% wt. DCPD seeding). Ca/P ratio varied from 1.0 to 1.67. Mixing of mineral powders and homogenization of liquid and solid phases were performed as previously described.

e) Typical Cement-Like Hybrid Compositions/Bio-Materials

Representative hybrid compositions for self-setting cement-like biomaterials are given in Tables 15-22.

Solid phases were calcium phosphates and calcium phosphates+organic powders grounded by ball milling, and mixed together by rotating or ball mixing. Liquid phase were thermo-gelling chitosan-GP solutions at 1 or 2% w/v chitosan. Liquid and solid phases were mixed homogeneously by hand mixing (spatula), then disposed in cylindrical flat-ended silicone molds (D×L=8 mm×16 mm) (see FIGS. 1 and 3).

Ultimate compressive strength of cement-like hybrid materials were determined on specimens that were shaped in cylindrical flat-ended silicone molds (D×L=8 mm×16 mm). Compositions were not compressed in molds prior to formation at 37° C. and mechanical testing (free formation). Specimens were aged for 15 days in an aqueous medium, and the specimen ends were flattened and paralleled by polishing. The cylindrical specimens were tested in compression to rupture on a MTS hydraulic mechanical testing machine, at a cross-head rate of 1 mm/min.

TABLE 14

Composition of liquid and solid phases for cement-like bio-materials

| Mineral Phase | Ca/P | Liquid Phase | L/S ml/g | Observations |
| --- | --- | --- | --- | --- |
| βTCP/OCP | 1.45 | Gelling CGP (C 1%) | 1.0 | Set.: 1 h; hard.: 3 (24 h) |
| | | Gelling CGP (C 1%), NaP 0.01M | 1.0 | Set.: 1 h; hard.: 3 (24 h) |
| | | Gelling CGP (C 1%) | 1.20 | Set.: 1 h; hard.: 4 (16 h) |
| TTCP/OCP | 1.66 | Gelling CGP (C 1%), NaP 0.01M | 1.20 | Set.: 1 h; hard.: 4 (16 h) |
| | | Gelling CGP (C 1%) | 1.20 | Set.: 1 h; hard.: 4 (16 h) |
| TTCP/OCP | 1.66 | Gelling CGP (C 1%), NaP 0.01M | 1.20 | Set.: 1 h; hard.: 4 (16 h) |
| MCPM/OCP/HAP | 1.25 | Gelling CGP (C 1%) | 0.9 | Set.: 3 h; hard.: 3 (5 h) |
| MCPM/OCP/CaO/HAP | 1.45 | Gelling CGP (C 1%) | 2.4 | Set.: 1 h; hard.: 2 (5 h) |
| MCPM/OCP/$CaCO_3$/HAP | 1.46 | Gelling CGP (C 1%) | 2.0 | Set.: 1 h; hard.: 2 (5 h) |
| MCPM/CaO/HAP | 1.56 | Gelling CGP (C 1%) | 1.4 | Set.: <1 h; hard.: 3 (1 h) |
| | | Gelling CGP (C 1%), NaP 0.01M | 1.4 | Set.: <1 h; hard.: 3 (1 h) |
| MCPM/CaO/HAP | 1.56 | Gelling CGP (C 1%) | 1.4 | Set.: <1 h; hard.: 3 (1 h) |
| | | Gelling CGP (C 1%), NaP 0.01M | 1.4 | Set.: <1 h; hard.: 3 (1 h) |
| MCPM/$CaCO_3$/HAP | 1.48 | Gelling CGP (C 1%) | 1.0 | Set.: 1 h; hard.: 4 (20 h) |
| MCPM/CaO/$CaCO_3$/HAP | 1.47 | Gelling CGP (C 1%) | 1.4 | Set.: 1 h; hard.: 4 (20 h) |
| HAP/CaO/ZnO/MCPM | 1.50 | Gelling CGP (C 1%) | 1.6 | Set.: 1 h; hard.: 4 (20 h) |
| DCPA/CaO/HAP | 1.46 | Gelling CGP (C 1%) | 0.8 | Set.: 1 h; hard.: 2 (24 h) |
| | | Gelling CGP (C 1%), NaP 0.01M | 0.8 | Set.: 1 h; hard.: 2 (24 h) |
| DCPA/CaO/$CaCO_3$/HAP | 1.66 | Gelling CGP (C 1%) | 0.8 | Set.: 1 h; hard.: 2 (24 h) |
| | | Gelling CGP (C 1%), NaP 0.01M | 0.8 | Set.: 1 h; hard.: 2 (24 h) |
| HAP/CaO/ZnO | 1.73 | Gelling CGP (C 1%) | 1.6 | Set.: 1 h; hard.: 2 (20 h) |
| HAP/CaO/ZnO/cit. ac | 1.73 | Gelling CGP (C 1%) | 1.6 | Set.: 1 h; hard.: 2 (20 h) |

S/L ratio: is given in ml of liquid phase per gram of solid phase.
Ca/P*: Total Ca/P ratio for solid phase.
Hardness: from 0 (liquid) to 5 (very hard).

TABLE 15

Composition of liquid and solid phases for self-setting hybrid compositions and bio-materials (TCP and TTCP based)

| # | Solid phase | Liquid phase (% in w/v) | Ca/P | L/S (mL/g) | Setting/Hardening |
|---|---|---|---|---|---|
| 1 | TTCP + MCPM | CGP, C 1%. | 1.66 | 0.55 | Suspension with limited homogeneity; Injectability difficult; Setting; Hardening (0-4 hrs). Hard after ageing. |
| 2 | TTCP + DCPA + MCPM | CGP, C 1%. | 1.50 | 0.6 | Fine & workable slurry; Injectability difficult; Setting Hardening (0-4 hrs). Hard after ageing. |
| 3 | TTCP + DCPA + Citric ac. | CGP, C 1%. | 1.66 | 0.32 | Fine & workable slurry; Injectability must be rapid; Setting rapid; Hardening (1 min). Hard after ageing. |
| 4 | βTCP + MCPM | CGP, C 1%. | 1.33 | 0.3 | Fine & workable slurry; Injectability must be rapid; Setting rapid; Hardening (1 min). Hard after ageing. |
| 5 | αTCP + MCPM + HA | CGP, C 1%. | 1.37 | 0.7 | Suspension with limited homogeneity; Injectability difficult; Setting; Hardening (0-6 hrs). Hard after ageing. |
| 6 | αTCP + DCPA + HA | CGP, C 1%. | 1.33 | 0.5 | Fine, flowable & workable slurry; Injectable; Setting; Hardening (0-6 hrs). Hard after ageing. |
| 7 | αTCP + citric ac. + HA | CGP, C 1%. | 1.50 | 0.4 | Fine, flowable & workable slurry; Injectable; Setting; Hardening (0-10 min.). Hard after ageing. |

TABLE 16

Ultimate compressive strengths (MPa) of self-setting hybrid materials (uncompressed specimens, TCP and TTCP based)

| # | Solid phase | Liquid Phase: Pure water | Liquid Phase: CGP, 1% chitosan | Liquid Phase: CGP, 2% chitosan |
|---|---|---|---|---|
| 1 | TTCP + MCPM | ND | 3.5 (0.2) | 3.20 (0.75) |
| 2 | TTCP + DCPA + MCPM | ND | 2.9 (1.0) | 3.4 (0.7) |
| 3 | TTCP + DCPA + citric ac. | 5.7 Mpa (0) | 6.8 (0.4) | 8.2 (2.3) |
| 4 | βTCP + MCPM | ND | 2.2 (0.5) | 1.3 (0.1) |
| 5 | αTCP + MCPM + HA | ND | 11.85 (2.00) | 13.4 (1.7) |
| 6 | αTCP + DCPA + HA | 10.1 Mpa (3.3) | 7.75 (1.50) | 17.85 (4.9) |
| 7 | αTCP + citric ac. + HA | 17.1 Mpa (2.5) | 29.00 (8.45) | 21.0 (8.0) |

ND: not determined;
( ): standard deviation

TABLE 17

Composition of liquid and solid phases for self-setting hybrid alpha-TCP based compositions and bio-materials (changes of apatitic charge)

| # | Solid phase (% wt.) | Liquid phase (% in w/v) | Ca/P | L/S (mL/g) | pH range (start.-final) | Setting/Hardening |
|---|---|---|---|---|---|---|
| 1 | αTCP + citric ac. (11.7%) + CDAc (10.0%) | CGP, Chitosan 1%. | 1.50 | 0.40 | 4.80-5.46 | Initial set.: 4 min Final set.: 8-10 min |
| 2 | αTCP + citrate (9.0%) + CDAc (10.0%) | CGP, Chitosan 1%. | 1.50 | 0.40 | 5.76-6.60 | Initial set.: 6 min Final set.: 30 min |
| 3 | αTCP + citrate (11.7%) + CDAc (10.0%) | CGP, Chitosan 1%. | 1.50 | 0.40 | 5.75-6.30 | Initial set.: 7 min Final set.: 30 min |
| 4 | αTCP + citrate (9.0%) + CDAh (10.0%) | CGP, Chitosan 1%. | 1.50 | 0.40 | 6.13-6.62 | Cohesion time: 8 min Initial set.: 9 min Final set.: 33 min Injectability is 100% |

TABLE 17-continued

Composition of liquid and solid phases for self-setting hybrid alpha-TCP based compositions and bio-materials (changes of apatitic charge)

| # | Solid phase (% wt.) | Liquid phase (% in w/v) | Ca/P | L/S (mL/g) | pH range (start.-final) | Setting/Hardening |
|---|---|---|---|---|---|---|
| 5 | αTCP + citrate (9.0%) + SHA (10.0%) | CGP, Chitosan 1%. | 1.50 | 0.40 | 6.02-6.59 | Cohesion time: 7 min<br>Initial set.: 9 min<br>Final set.: 33 min<br>Injectability is 100% |

CDAc: Calcium Deficient Apatite, commercial, Ca/P = 1.5;
CDAh: Calcium Deficient Apatite, home synthesized, Ca/P = 1.5;
SHA: Sintered Hydroxyapatite, commercial;
pH (start.-final): pH after preparation of slurry-pH after setting (>8 hrs)

TABLE 18

Setting and injectability of an alpha-TCP based self-setting Composition

| # | Solid phase (charge, % wt.) | L/S = 0.30 mL/g | L/S = 0.40 mL/g | L/S = 0.50 mL/g |
|---|---|---|---|---|
| 1 | CDAc 0.0% | CT: 2.5 min<br>In. set.: 2.5 min<br>Fin set.: 9.5 min<br>Inj.: 0% | CT: 8.0 min<br>In. set.: 10.5 min<br>Fin set.: 32 min<br>Inj.: 100% | CT: 24.0 min<br>In. set.: 44.0 min<br>Fin set.: 110 min<br>Inj.: 100% |
| 2 | CDAc 5.0% | CT: 3.0 min<br>In. set.: 3.5 min<br>Fin set.: 8.0 min<br>Inj.: 0% | CT: 8.0 min<br>In. set.: 11.5 min<br>Fin set.: 32 min<br>Inj.: 80-100% | CT: 30.0 min<br>In. set.: 33.0 min<br>Fin set.: 85 min<br>Inj.: 100% |
| 3 | CDAc 10.0% | CT: 8.0 min<br>In. set.: 4.0 min<br>Fin set.: 6.5 min<br>Inj.: 0% | CT: ND<br>In. set.: 7 min<br>Fin set.: 30 min<br>Inj.: ND | CT: 17.0 min<br>In. set.: 22.0 min<br>Fin set.: 44 min<br>Inj.: 100% |
| 4 | CDAc 15.0% | CT: 3.0 min<br>In. set.: 5.5 min<br>Fin set.: 14.0 min<br>Inj.: 70% | CT: 5.0 min<br>In. set.: 10.0 min<br>Fin set.: 28 min<br>Inj.: 90-100% | CT: 11.0 min<br>In. set.: 12.0 min<br>Fin set.: 34 min<br>Inj.: 90-100% |
| 5 | CDAc 20.0% | CT: 3.0 min<br>In. set.: 4.5 min<br>Fin set.: 11.0 min<br>Inj.: 0% | CT: 3.0 min<br>In. set.: 5.0 min<br>Fin set.: 23 min<br>Inj.: 0% | CT: ND<br>In. set.: 13.0 min<br>Fin set.: 40 min<br>Inj.: 80-100% |
| 6 | CDAc 50.0% | | CT: 4.0 min<br>In. set.: 8.5 min<br>Fin set.: 36 min<br>Inj.: 0% | |

(Liquid: chitosan-glycerophosphate-water, chitosan 1% w/v);
(Solid: alpha-TCP, CDAc 10% wt., citrate 9% wt.).

Figure 4:
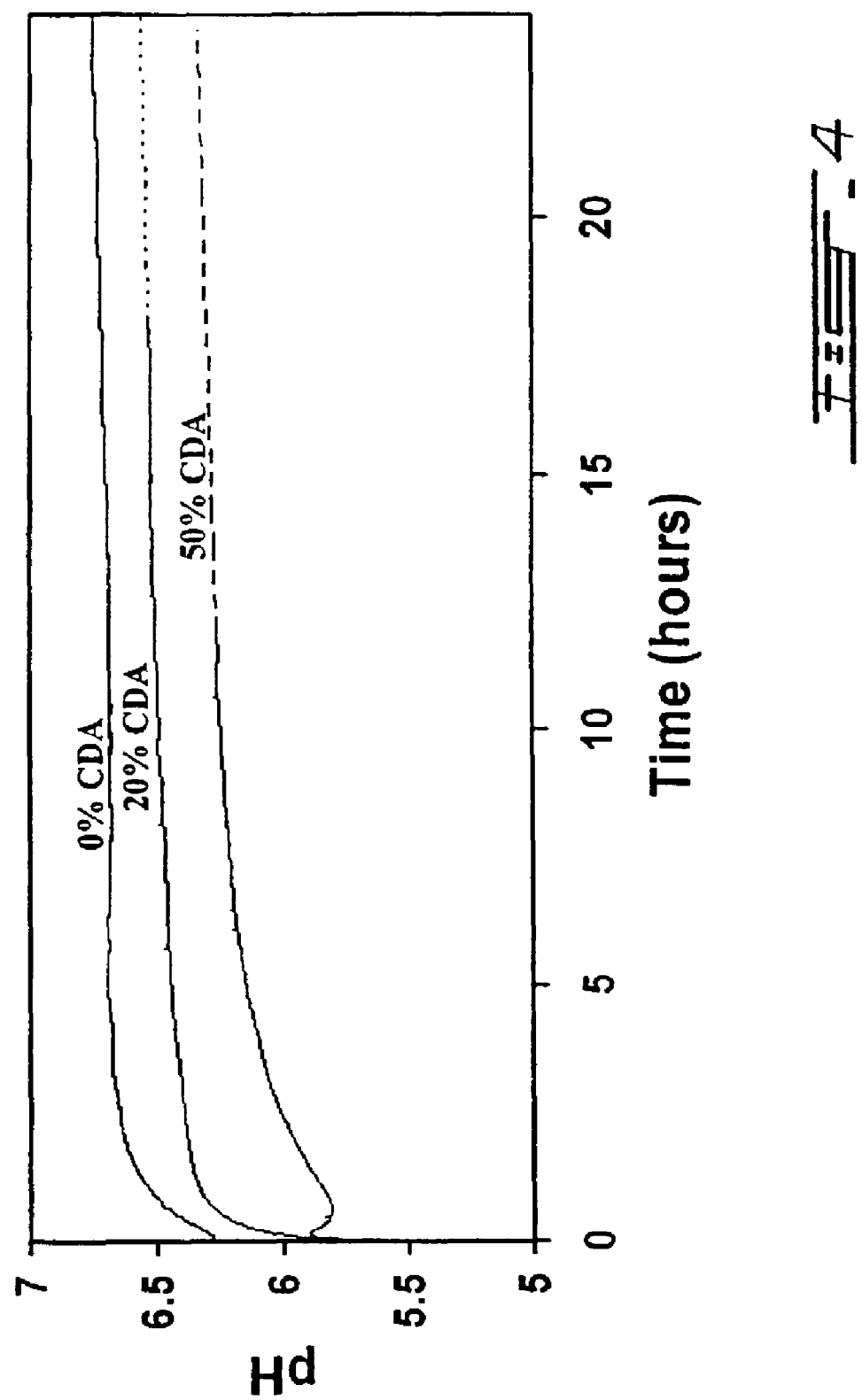
FIG. 4 illustrates the pH evolution during the setting of a mineral-polymer hybrid composition of the present invention.

TABLE 19 pH change of an alpha-TCP based self-selling Composition (see FIG. 4)

| # | Solid phase (charge, % wt.) | L/S = 0.30 mL/g | L/S = 0.40 mL/g | L/S = 0.50 mL/g |
|---|---|---|---|---|
| 1 | CDAc 0.0% | pH start: 6.09<br>pH final: 6.70 | pH start: 6.27<br>pH final: 6.75 | pH start: 6.02<br>pH final: 6.65 |
| 2 | CDAc 5.0% | pH start: 6.11<br>pH final: 6.66 | | |
| 3 | CDAc 10.0% | pH start: 6.06<br>pH final: 6.70 | pH start: 5.76<br>pH final: 6.60 | pH start: 5.97<br>pH final: 6.55 |
| 4 | CDAc 15.0% | pH start: 6.04<br>pH final: 6.68 | | |
| 5 | CDAc 20.0% | pH start: 5.84<br>pH final: 6.62 | pH start: 5.76<br>pH final: 6.56 | |
| 6 | CDAc 50.0% | | pH start: 5.73<br>pH final: 6.30 | |

CDAc: Calcium Deficient Apatite, commercial, Ca/P = 1.50;
CT: cohesion time (in min)
In. set.: initial setting (in min)
Fin set.: final setting (in min)
Inj.: injectability (capacity to be injected)
pH (start.-final): pH after preparation of slurry-pH after setting (>8 hrs)

TABLE 20

Figure 5:
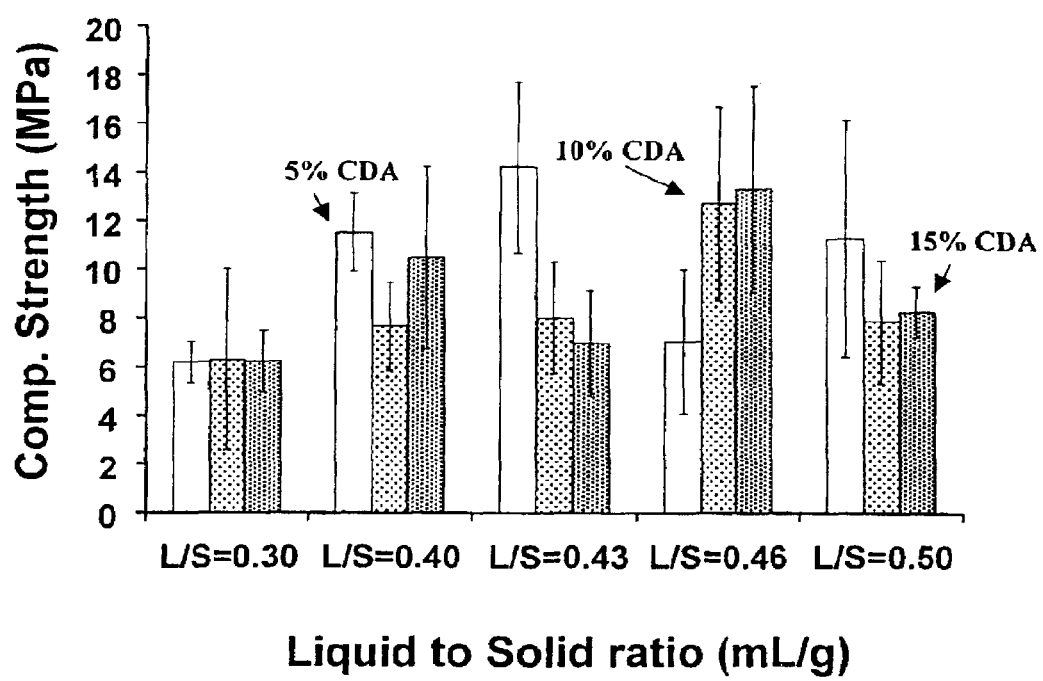
FIG. 5 illustrates the evolution of the ultimate compression strength (Megapascals, Mpa) of a mineral-polymer hybrid composition (calcium deficient apatite with a Ca/P ratio of 1.50) as a function of L/S and percent charge (weight).

Ultimate compression strengths of an alpha-TCP based self-setting Composition (see FIG. 5)

| # | Solid phase (charge, % wt.) | L/S = 0.30 mL/g | L/S = 0.40 mL/g | L/S = 0.50 mL/g |
|---|---|---|---|---|
| 1 | CDAc 0.0% | 7.67 (1.58) | 7.36 (2.25) | 11.74 (1.79) |
| 2 | CDAc 5.0% | 6.18 (0.84) | 11.50 (1.61) 2-days<br>7.75 (2.60) 7-days<br>9.50 (3.33) 28-days | 11.30 (4.87) |
| 3 | CDAc 10.0% | 6.28 (3.70) | 7.66 (1.78) | 7.86 (2.53) |
| 4 | CDAc 15.0% | 6.23 (1.28) | 10.47 (2.73) 2-days<br>9.50 (3.92) 7-days<br>11.06 (2.47) 28-days | 8.26 (1.02) |
| 5 | CDAc 20.0% | 6.88 (2.34) | 12.26 (4.00) | 7.26 (2.49) |
| 6 | CDAc 50.0% | ND | 3.55 (0.56) | ND |

CDAc: Calcium Deficient Apatite, commercial, Ca/P = 1.50;
ND: not determined;
( ): standard deviation
(Liquid: chitosan-glycerophosphate-water, chitosan 1% w/v);
(Solid: alpha-TCP, CDAc 10% wt., citrate 9% wt.).

TABLE 21

Setting and injectability of an alpha-TCP/Calcium Carbonate based self-setting Composition

| # | Solid phase Liquid phase* (charge, % wt.) | 1 CaCO$_3$ 5.9% | 2 CaCO$_3$ 10.0% | 3 CaCO$_3$ 9.15% | 4 CaCO$_3$ 20.0% |
|---|---|---|---|---|---|
| 1 | αTCP CDAc 15.0% Citrate 9.0% L/S = 0.4 mL/g | CT: 9.0 min In. set.: 12.0 min Fin set.: 44.0 min Inj.: 0% pH: 5.7-6.6 | | | |
| 2 | αTCP CDAc 15.0% Citrate 9.0% L/S = 0.4 mL/g | | CT: 5.0 min In. set.: 13.0 min Fin set.: 27.0 min Inj.: 100% | | |
| 3 | αTCP CDAc 15.0% Citric ac. 11.7% L/S = 0.4 mL/g | | | CT: 6.0 min In. set.: 4.0 min Fin set.: 12.0 min Inj.: 5-10%% pH: 4.8-6.03 | |
| 4 | αTCP CDAc 15.0% Citric ac. 11.7% L/S = 0.4 mL/g | | | | CT: 5.0 min In. set.: 4.0 min Fin set.: 12.0 min Inj.: 100% pH: 4.7-6.3 |

CDAc: Calcium Deficient Apatite, commercial, Ca/P = 1.50;
CT: cohesion time (in min)
In. set.: initial setting (in min)
Fin set.: final setting (in min)
Inj.: injectability (capacity to be injected)
pH (start.-final): pH after preparation of slurry-pH after setting (>8 hrs)
(Liquid: chitosan-glycerophosphate-water, chitosan 1% w/v);

TABLE 22 pH change of an alpha-TCP/Calcium Carbonate based self-setting Composition

| # | Solid phase Liquid Phase (charge, % wt.) | 1 CaCO$_3$ 5.9% | 2 CaCO$_3$ 10.0% | 3 CaCO$_3$ 9.15% | 4 CaCO$_3$ 20.0% |
|---|---|---|---|---|---|
| 1 | αTCP CDAc 15.0% Citrate 9.0% L/S = 0.4 mL/g | 4.55 (1.22) | | | |
| 2 | αTCP CDAc 15.0% Citrate 9.0% L/S = 0.4 mL/g | | 4.94 (0.33) | | |
| 3 | αTCP CDAc 15.0% Citric ac. 11.7% L/S = 0.4 mL/g | | | 17.35 (3.07) | |
| 4 | αTCP CDAc 15.0% Citric ac. 11.7% L/S = 0.4 mL/g | | | | 12.85 (3.96) |

CDAc: Calcium Deficient Apatite, commercial, Ca/P = 1.50;
ND: not determined;
( ): standard deviation While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An injectable self-setting composition comprising:
    a) a liquid component, free of insoluble material, comprising, an organic and/or inorganic acid, a partially N-deacetylated chitosan and/or a collagen, and a glycerophosphate salt; said liquid component having a pH ranging from 6.5 to 7.4, said liquid component having an endothermally gelling character, said partially N-deacetylated chitosan having a final concentration ranging between 0.5 to 3.0% w/v, and said glycerophosphate salt having a final concentration ranging between 1.0 to 10.0% w/v, and
    b) a powder component comprising a dry mixture of a tricalcium phosphate with a calcium deficient apatite or an octacalcium phosphate, and with at least one of an inorganic salt, an organic salt, an organic acid source and an organic compound,
    wherein when said components of step a) and b) are intimately and uniformly mixed together, said components of step a) and b) form an injectable thermo-setting slurry, said slurry when heated turns into a solid material.

2. The composition as described in claim 1, wherein said inorganic salt is selected from carbonate, phosphate, strontium, and fluoride salts.

3. The composition as described in claim 1, wherein said organic salt is selected from citrate, malate, lactate, and gluconate salts.

4. The composition as described in claim 1, wherein said organic acid is selected from citric acid, malic acid, lactic acid, and gluconic acid.

5. The composition as described in claim 1, wherein said organic compound is selected from the group consisting of biological fluids and components, water-soluble or miscible organic polyols, drugs, aminoacids, and proteins.

6. The composition as described in claim 1, which further comprises a water-soluble or miscible organic polyol, including sugar-polyol, saccharide-polyol and glycol, selected from the group consisting of glycerol, mannitol, sorbitol, ethylene glycol oligomers, propylene glycol oligomers, saccharose, fructose, glucose, and maltose.

7. The composition as described in claim 1, which further comprises glucosamine and/or histidine.

8. The composition as described in claim 1, which further comprises a strontium containing compound.

9. The composition as described in claim 1, which further comprises a carbonate containing compound.

10. The composition as described in claim 1, which further comprises a fluoride containing compound.

* * * * *